(12) United States Patent
Sanborn

(10) Patent No.: US 11,183,269 B2
(45) Date of Patent: Nov. 23, 2021

(54) SYSTEMS AND METHODS FOR TUMOR CLONALITY ANALYSIS

(71) Applicant: Five3 Genomics, LLC, Santa Cruz, CA (US)

(72) Inventor: John Zachary Sanborn, Santa Cruz, CA (US)

(73) Assignee: Five3 Genomics, LLC, Culver City, CA (US)

(*) Notice: Subject to any disclaimer, the term of this patent is extended or adjusted under 35 U.S.C. 154(b) by 534 days.

(21) Appl. No.: 14/434,397

(22) PCT Filed: Nov. 7, 2013

(86) PCT No.: PCT/US2013/064081
§ 371 (c)(1),
(2) Date: Apr. 8, 2015

(87) PCT Pub. No.: WO2014/058987
PCT Pub. Date: Apr. 17, 2014

(65) Prior Publication Data
US 2015/0261912 A1    Sep. 17, 2015

Related U.S. Application Data

(60) Provisional application No. 61/711,467, filed on Oct. 9, 2012.

(51) Int. Cl.
*G16B 20/20* (2019.01)
*G16B 20/00* (2019.01)
(Continued)

(52) U.S. Cl.
CPC ............. *G16B 20/20* (2019.02); *G16B 20/00* (2019.02); *G16B 30/00* (2019.02); *G16B 30/10* (2019.02);
(Continued)

(58) Field of Classification Search
None
See application file for complete search history.

(56) References Cited

U.S. PATENT DOCUMENTS

2009/0246779 A1   10/2009  Rabinovitch et al.
2010/0274495 A1   10/2010  Sobol
(Continued)

FOREIGN PATENT DOCUMENTS

AU   2013329356 B2   11/2018
AU   2019201246 A1    3/2019
(Continued)

OTHER PUBLICATIONS

W Liu et al. Copy number analysis indicates monoclonal origin of lethal metastatic prostate cancer. Nature Medicine, 2009, vol. 15, No. 5, p. 559-565 (Year: 2009).*

(Continued)

*Primary Examiner* — Olivia M. Wise
(74) *Attorney, Agent, or Firm* — Martin Fessenmaier; Umberg Zipser LLP

(57) ABSTRACT

Systems and methods of genomic analysis are presented that provide a framework to determine a tumor's clonality, the number and proportion of all major clones, and the variants that distinguish them. Contemplated systems and methods also allow phasing mutations to parental alleles to so time their emergence within the population of tumor cells, and provide an accurate estimate of the amount of contaminating normal tissue that was present in the tumor biopsy.

16 Claims, 13 Drawing Sheets

(51) Int. Cl.
G16B 30/00 (2019.01)
G16B 30/10 (2019.01)
G16B 40/00 (2019.01)
G16B 20/10 (2019.01)

(52) U.S. Cl.
CPC ........ *C12Q 2600/156* (2013.01); *G16B 20/10* (2019.02); *G16B 40/00* (2019.02)

(56) References Cited

U.S. PATENT DOCUMENTS

| | | | |
|---|---|---|---|
| 2011/0111419 | A1 | 5/2011 | Stefansson et al. |
| 2011/0118145 | A1 | 5/2011 | Akmaev et al. |
| 2011/0301854 | A1* | 12/2011 | Curry .................. C12Q 1/6827 702/19 |
| 2012/0059670 | A1* | 3/2012 | Sanborn .................. G06F 19/22 705/3 |
| 2012/0208706 | A1 | 8/2012 | Downing et al. |
| 2012/0220466 | A1 | 8/2012 | Fire et al. |
| 2018/0157791 | A1 | 6/2018 | Sanborn et al. |

FOREIGN PATENT DOCUMENTS

| | | |
|---|---|---|
| CA | 2 892 308 A1 | 4/2014 |
| CN | 104885090 A | 9/2015 |
| EP | 2 907 062 B1 | 5/2020 |
| IN | 3223/DELN/2015 A | 10/2015 |
| JP | 2004-527211 A | 9/2004 |
| JP | 2009-529326 A | 8/2009 |
| JP | 2012-165736 A | 9/2012 |
| JP | 2013-510580 A | 3/2013 |
| JP | 2013-531980 A | 8/2013 |
| JP | 2015-531240 A | 11/2015 |
| KR | 2015-0093658 A | 8/2015 |
| WO | 02/12447 A2 | 2/2002 |
| WO | 2006110855 A2 | 10/2006 |
| WO | 2007/101979 A2 | 9/2007 |
| WO | 2011/060240 A1 | 5/2011 |
| WO | 2011/149534 A2 | 12/2011 |
| WO | 2011149534 | 12/2011 |
| WO | 2012/119013 A1 | 9/2012 |
| WO | 2013074058 | 5/2013 |
| WO | 2013166517 | 11/2013 |
| WO | 2014026096 | 2/2014 |
| WO | 2014/058987 A1 | 4/2014 |
| WO | 2014/058987 A4 | 6/2014 |

OTHER PUBLICATIONS

P Van Loo et al. Allele-specific copy number analysis of tumors. PNAS, 2010, vol. 107, No. 39, p. 16910-16915 (Year: 2010).*
LK Boyd et al. High-resolution genome-wide copy-number analysis suggests a monoclonal origin of multifocal prostate cancer. Genes, Chromosomes & Cancer, 2012, 51:579-589 (Year: 2012).*
Turner et al. Genetic heterogeneity and cancer drug resistance. Lancet Oncol Apr. 2012, 13, e178-85 (Year: 2012).*
ISA/KR, International Search Report and Written Opinion for International Application No. PCT/US2013/064081, dated Mar. 12, 2014, 16 pages.
Rasmussen et al., "Allele-specific copy number analysis of tumor samples with aneuploidy and tumor heterogeneity", Genome Biology, Biomed Central Ltd., London, GB, (Oct. 24, 2011), vol. 12, No. 10, doi:10.1186/GB-2011-12-10-R108, ISSN 1465-6906, p. 10PP.
Parisi et al, "Detecting copy number status and uncovering subclonal markers in heterogeneous tumor biopsies", BMC Genomics 2011, 12:230.
Sanborn et al., "Tumor versus matched-normal sequencing analysis and data integration", UC Santa Cruz Electronic Theses and Dissertations, 2012, pp. 1-139, published on Dec. 31, 2012.
Govindan et al., "Genomic Landscape of Non-Small Cell Lung Cancer in Smokers and Never Smokers" National Institute of Health, Sep. 14, 2012, pp. 1121-1134.
Parisi, F., Detecting copy number status and uncovering subclonal markers in heterogeneous tumor biopsies, BMC Genomics, 2011, pp. 1-14, 12:230.
Rasmussen, M., Allele-specific copy number analysis of tumor samples with aneuploidy and tumor heterogeneity, Genome Biology, 2011, pp. 1-10, 12:R108.
Biorklund et al., "On Heterogeneity of Non-Hodgkin's Lymphomas as Regards Sensitivity to Cytostatic Drugs", European Journal of Cancer, vol. 16, pp. 634-647.
Examination report No. 1 received for Australian Patent Application Serial No. 2013329356 dated Sep. 18, 2018, 4 pages.
Notice of acceptance received for Australian Patent Application Serial No. 2013329356 dated Nov. 19, 2018, 3 pages.
Office Action received for Canadian Patent Application Serial No. 2892308 dated Sep. 27, 2019, 4 pagees.
Extended European Search Report received for European Patent Application Serial No. 13845204.0 dated Nov. 16, 2016, 11 pages.
Communication pursuant to Article 94(3) EPC received for European Patent Application Serial No. 13845204.0 dated Nov. 5, 2018, 6 pages.
Communication pursuant to Article 94(3) EPC received for European Patent Application Serial No. 13845204.0 dated May 17, 2019, 6 pages.
Communication under Rule 71(3) EPC received for European Patent Application Serial No. 13845204.0 dated Dec. 4, 2019, 7 pages.
Notice of Opposition received for European Patent Application Serial No. 13845204.0 dated Mar. 5, 2021, 12 pages.
Notification of Defects received for Israeli Patent Application Serial No. 238178 dated Mar. 12, 2019, 6 pages (Including English Translation).
Notice before Acceptance received for Israeli Patent Application Serial No. 238178 dated Mar. 11, 2020, 6 pages (Including English Translation).
Notice of Reasons for Refusal received for Japanese Patent Application Serial No. 2015536855 dated Oct. 24, 2017, 8 pages (Including English Translation).
Notice of Reasons for Refusal received for Japanese Patent Application Serial No. 2015536855 dated Jul. 3, 2018, 13 pages (Including English Translation).
Decision of Refusal received for Japanese Patent Application Serial No. 2015536855 dated Mar. 26, 2019, 11 pages (Including English Translation).
International Preliminary Report on Patentability Chapter II received for International Application Serial No. PCT/US2013/064081, dated Jan. 30, 2015, 17 pages.
First Office Action received for Chinese Patent Application Serial No. 201380061475.5 dated Dec. 29, 2016, 26 pages (Including English Translation).
Rejection Decision received for Chinese Patent Application Serial No. 201380061475.5 dated Aug. 24, 2018, 24 pages (Including English Translation).
Misale et al., "Emergence of KRAS mutations and acquired resistanceto anti EGFR therapy in colorectal cancer", Nature, 2012, 36 pages.
Second Office Action received for Chinese Patent Application Serial No. 201380061475.5 dated Aug. 28, 2017, 15 pages (Including English Translation).
Third Office Action received for Chinese Patent Application Serial No. 201380061475.5 dated Feb. 12, 2018, 17 pages (Including English Translation).

* cited by examiner

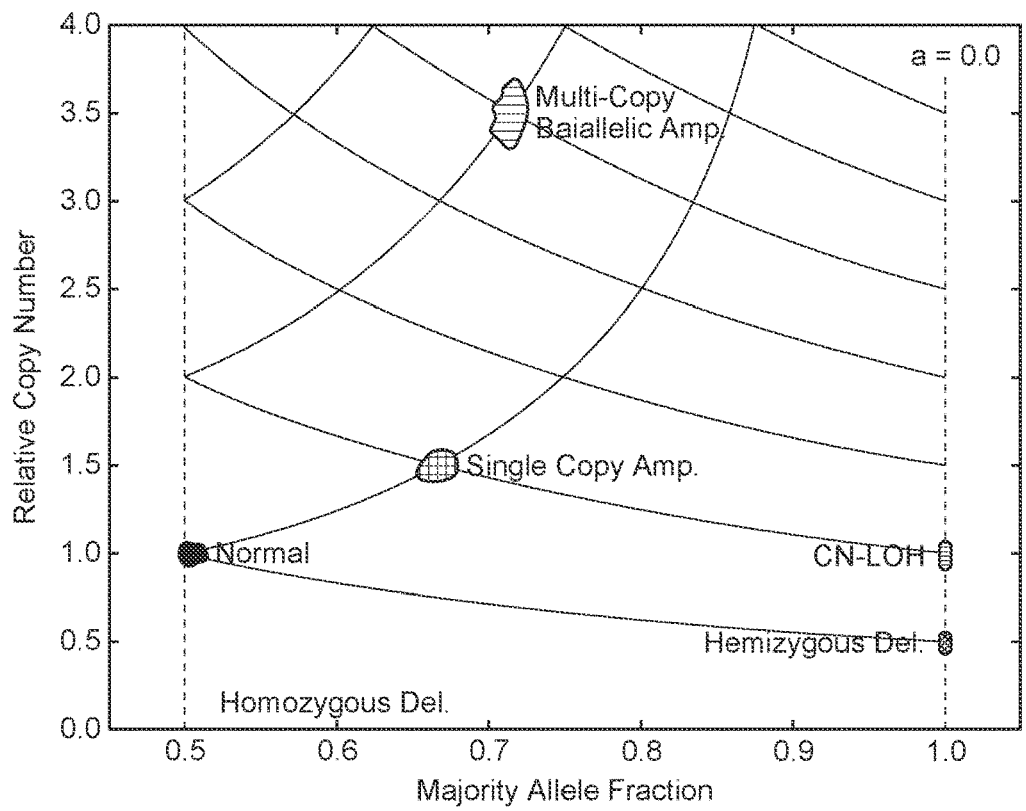
FIG. 3A
FIG. 3B
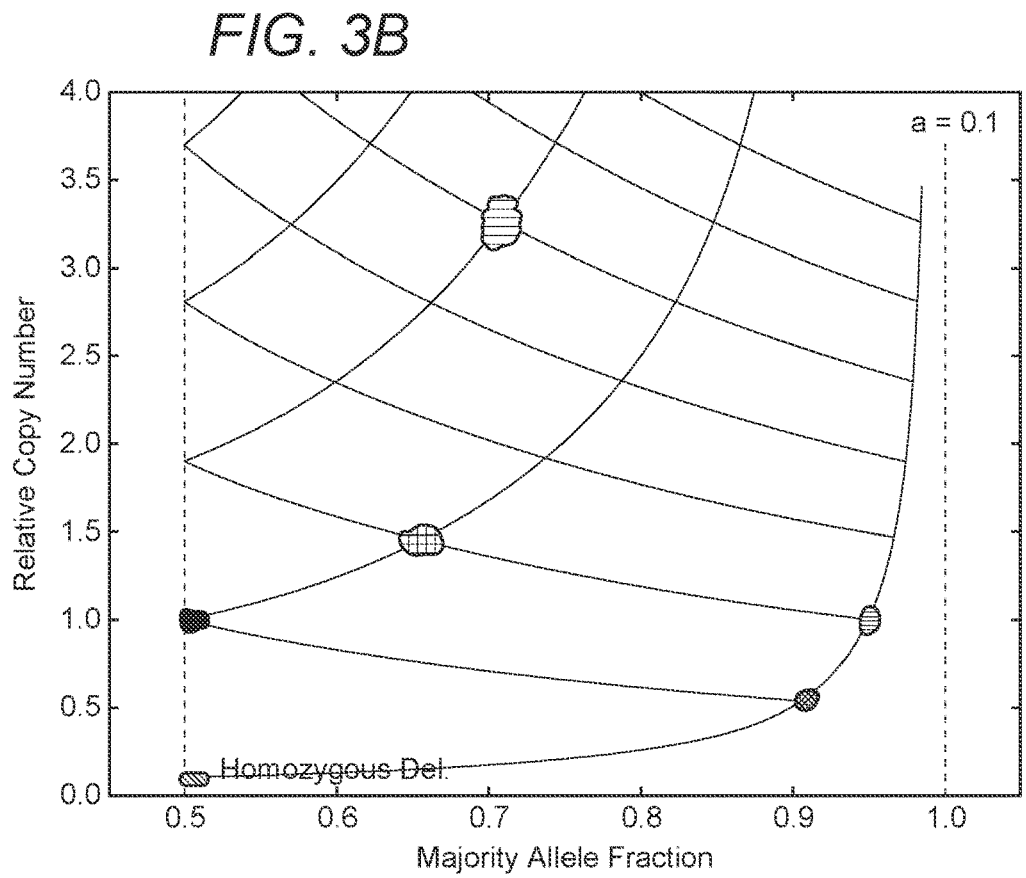

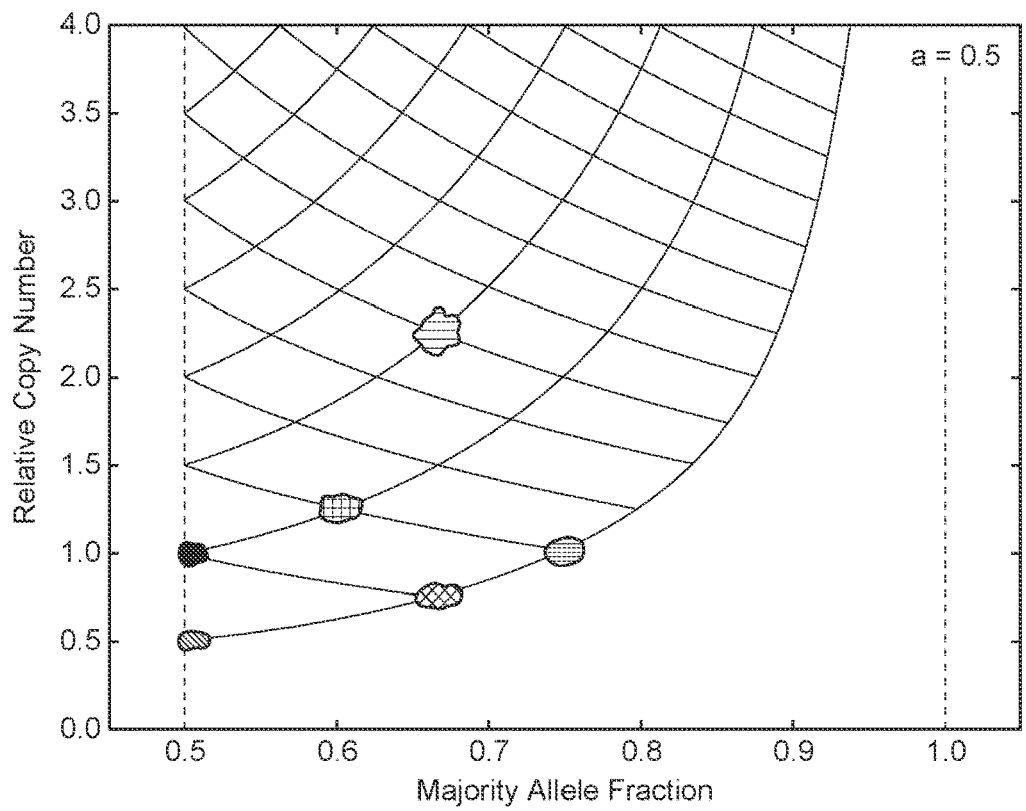
FIG. 3C
FIG. 3D
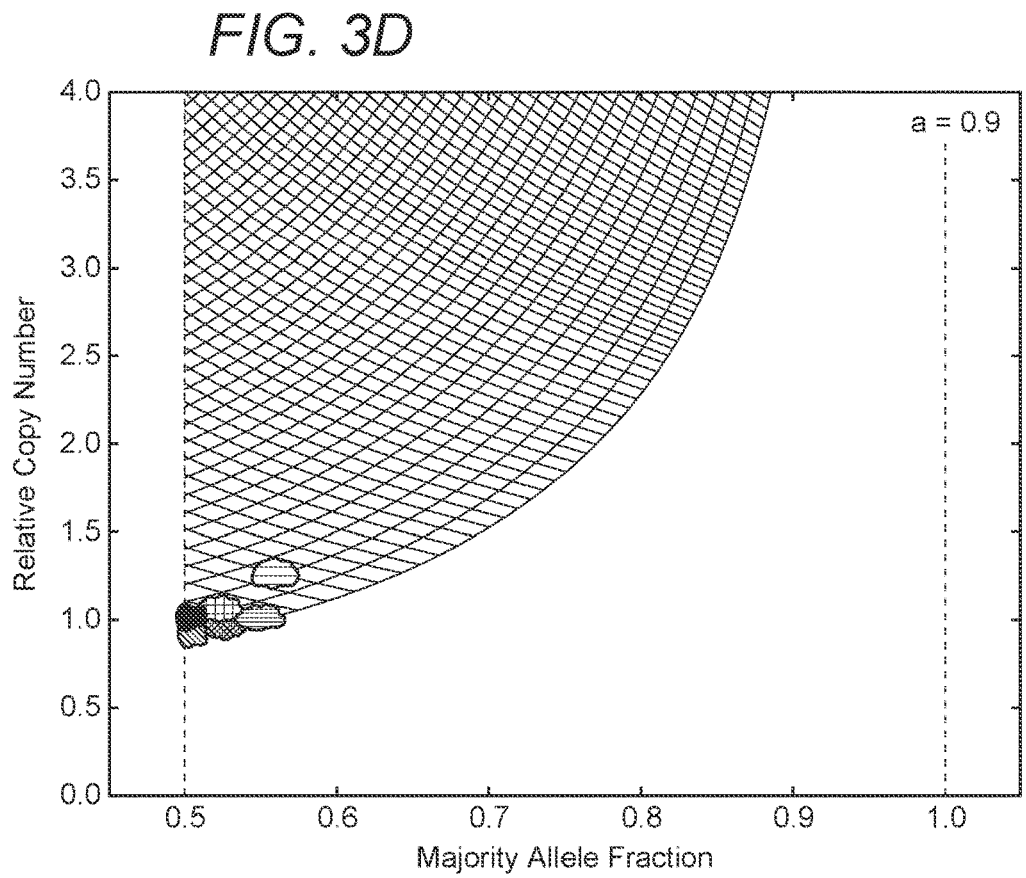

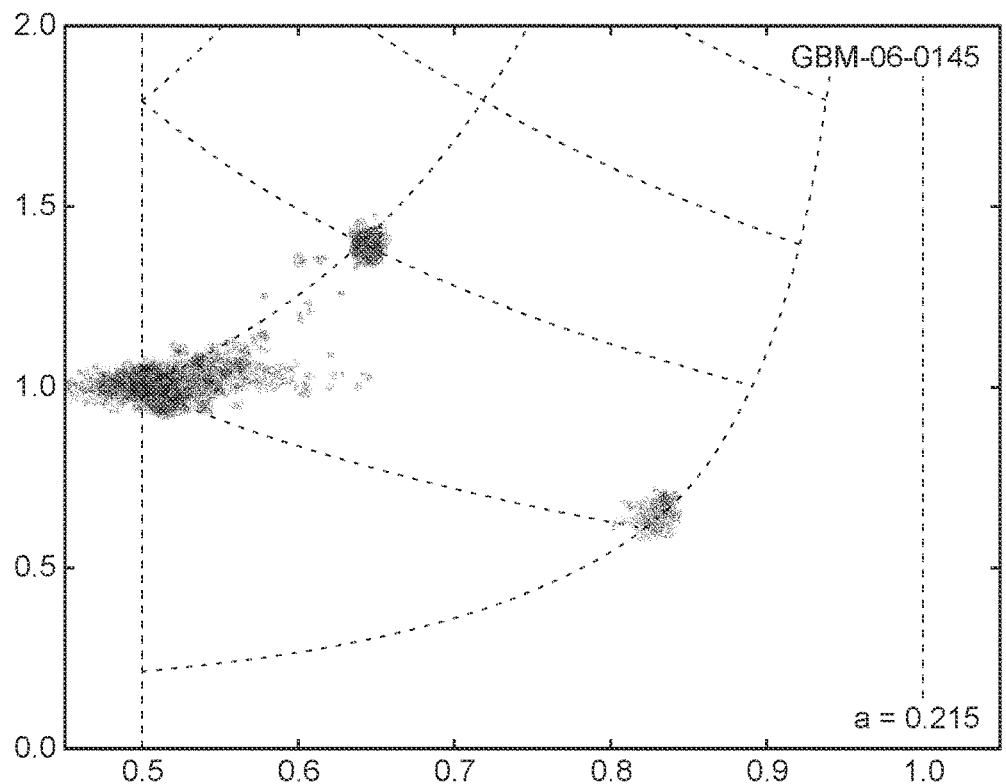
FIG. 7A
FIG. 7B
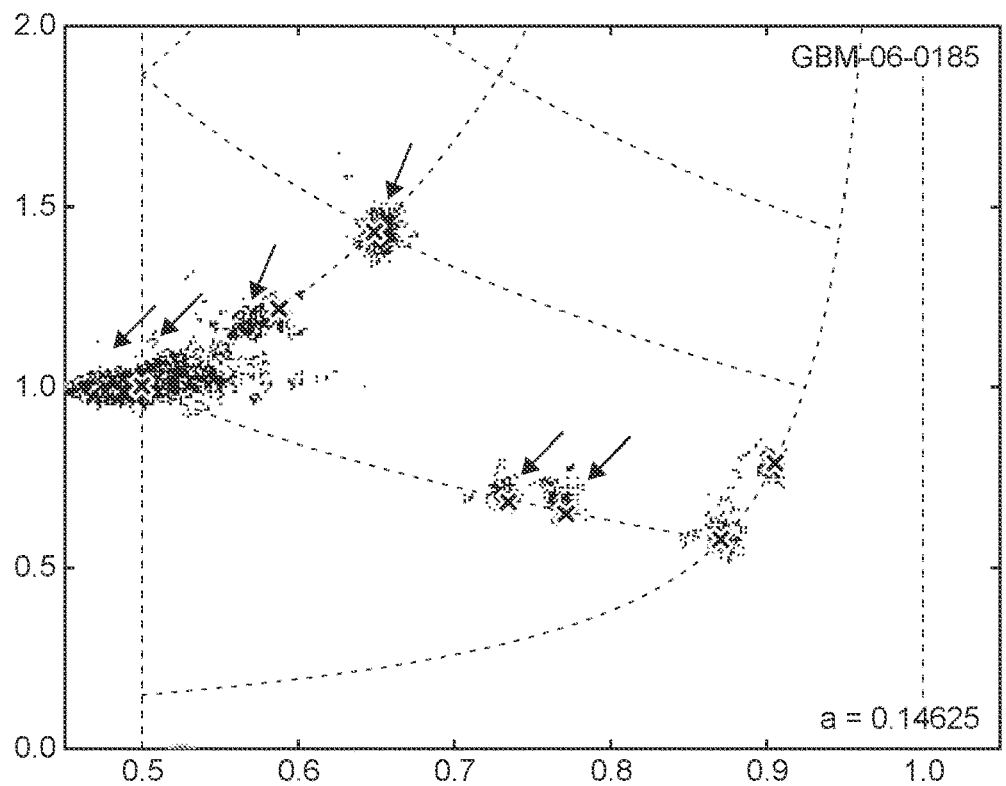

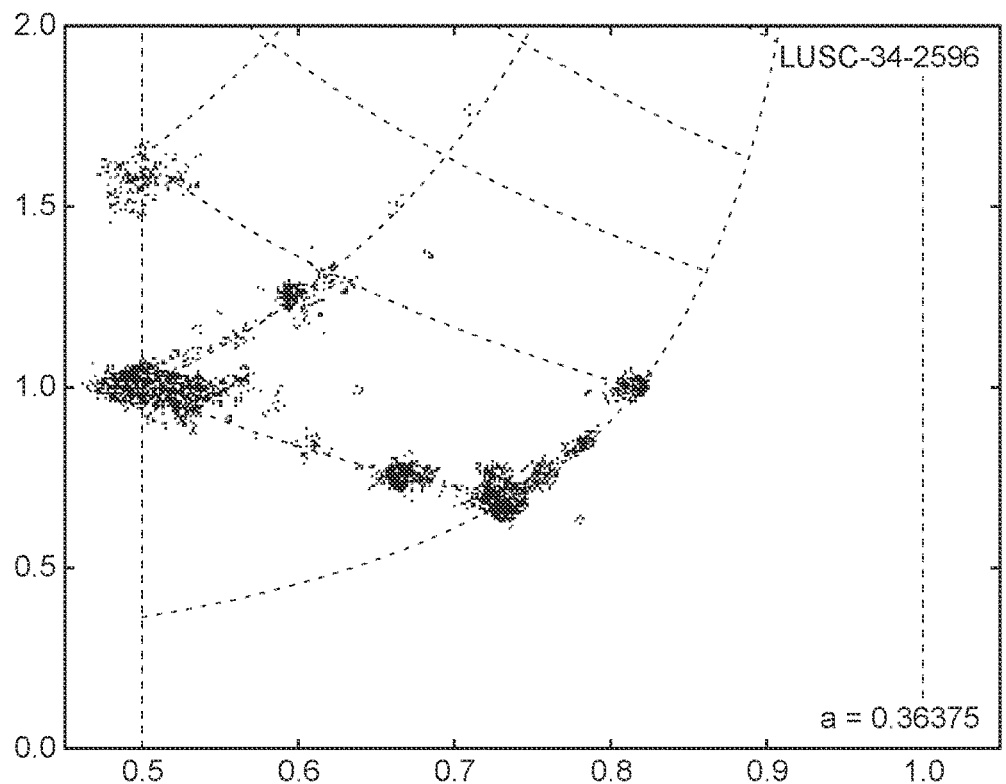
FIG. 7C
FIG. 7D
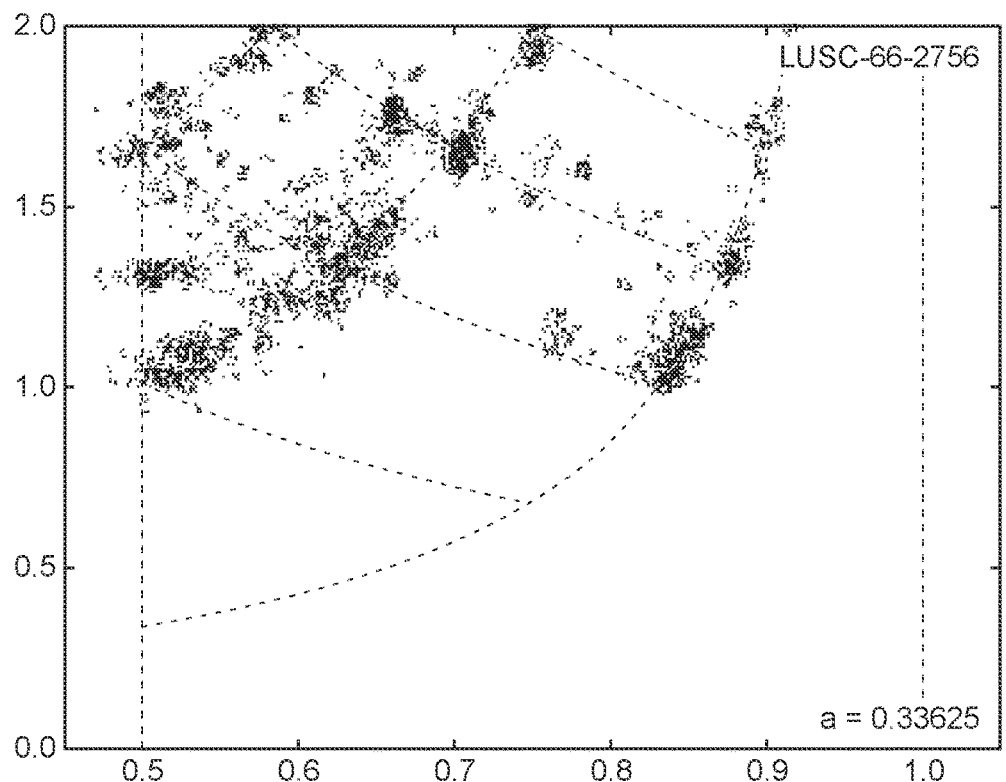

SYSTEMS AND METHODS FOR TUMOR CLONALITY ANALYSIS

This application claims priority to our U.S. provisional application with the Ser. No. 61/711,467, which was filed Oct. 9, 2012.

FIELD OF THE INVENTION

The field of the invention is computational analysis of genomic data, particularly as it relates to identification of clonality status of a mixed cell population.

BACKGROUND OF THE INVENTION

With the increasing availability of whole genome data and the ever-increasing speed of whole genome sequencing, enormous quantities of data are now available that demand a meaningful analysis to so provide a clinician or scientist with information to enable more effective treatment or drug development.

For example, multiple tumor and matched normal whole genome sequences are now available from projects like 'The Cancer Genome Atlas' (TCGA), and extraction of relevant information is difficult. This is further compounded by the need for high genome sequencing coverage (e.g., greater than 30-fold) to obtain statistically relevant data. Even in compressed form, such genomic information can often reach hundreds of gigabytes, and a meaningful analysis comparing multiple of such large datasets is in many cases very slow and difficult to manage, however, absolutely necessary to discover the many genomic changes that occurred in any given sample relative to a second sample. More recently, systems and methods have been developed to allow for rapid generation of information in a format that avoids massive output files as is described in WO2013/074058. This publication and all other publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

While the system of the '058 application provides a significant improvement over other known systems, various difficulties nevertheless are present. For example, most breast cancer is clinically and gnomically heterogeneous and is composed of several pathologically and molecularly distinct subtypes, which often complicates genomic analysis. Moreover, currently known methods do not allow for deconvolution of such genomic diversity to so gain insight into possible tumor cell evolution and resulting clonality among tumor cells in a tissue.

Thus, even though numerous methods of genomic analysis are known in the art, all or almost all of them suffer from several disadvantages. Most significantly, heretofore known methods fail to allow identification of tumor progression on a molecular level, and with that fail to provide insight into clonality and potential treatment efficacies. Viewed from another perspective, heretofore known methods failed to allow identification of clonality and clonal relationship of cell populations within a sample containing multiple non-homogenous cells. Consequently, there is still a need to provide improved systems and methods for genomic analysis, and especially systems and methods that provide information on clonality, clonal fraction, molecular tumor progression, and/or treatment options based on such information.

SUMMARY OF THE INVENTION

The present invention is directed to various systems, devices, and methods for genetic analysis, and especially genomic analysis to identify presence and distribution of distinct cell clones within a sample containing one or more clonal populations of cells based on genomic data obtained from the sample. In especially preferred aspects, analysis is based on genomic DNA from a tumor or otherwise abnormal cell population, and allows not only determination of multiple clones within the tumor or cell population but also allows identification of likely clonal evolution and/or clonal relationships.

In one aspect of the inventive subject matter, a method of ex-vivo determining clonality of a tumor from sequencing data obtained from the tumor includes a step of determining from the sequencing data copy number and allele fraction for an allele within the sequencing data, and another step of calculating an allelic state for the allele based on the determined copy number and the determined allele fraction. The allelic state is then used to determine the clonality of the tumor. While not limiting to the inventive subject matter, it is generally preferred that the allelic state is plotted or displayed in an allelic state diagram (which may be a single or dual allelic state diagram).

In at least some embodiment of the inventive subject matter determination of the copy number and allele fraction is performed by a sequence analysis program that produces local alignments by incremental synchronization of sequence strings (e.g., BAMBAM). Among other states, contemplated allelic states include normal copy number, single copy amplification, single copy/hemizygous deletion, copy-neutral loss of heterozygosity, and amplification of both alleles.

In further contemplated embodiments of the inventive subject matter, the allelic state calculation comprises a correction for normal contamination, uses majority and minority allelic states for tumor and normal, and/or includes an identification of a mixture fraction $M_b$ for an allele (which is either 0 or 1 for a monoclonal tumor, or greater than 0 and smaller than 1 when the tumor is polyclonal). It is still further contemplated that the calculation of the allelic state may also comprises a correction for sequencing coverage level, particularly where the coverage level for the tumor is higher than the coverage level for a corresponding non-tumor (e.g., healthy) sample of the same patient.

Where desired, contemplated methods will further include a step of determination of an allelic state landmark, which is preferably used to determine a number of distinct (related or unrelated) clones in the tumor and/or a proportion of clones in the tumor. Additionally, or alternatively, it is still further contemplated that a mutation can be linked to a majority allele or a minority allele, and that the mutational allele fraction can be employed for determination of timing of the mutation relative to a change in allelic state.

In another aspect of the inventive subject matter, a method of ex-vivo visualization of allelic states in a tumor includes a step of determining a copy number and an allele fraction for an allele within sequencing data, and a step of calculating the allelic state for the allele based on the determined copy number and the determined allele fraction. In a still further step, the allelic state of the allele is mapped in an allelic state diagram that plots copy number versus allele fraction (typically majority allele fraction).

Most typically, the allelic state diagram is presented such that each vertex in the allelic state diagram corresponds to a tumor allelic state, that clones with loss or gain of an allele in a polyclonal tumor map along edges drawn between vertices, and/or that clones with changes other than loss or gain of an allele in a polyclonal tumor map between edges drawn between vertices. It is still further contemplated that the allelic state diagram is adjusted for normal contamination. Of course, it should be appreciated that the allelic state diagram may be a dual allele state diagram.

Therefore, and viewed from a different perspective, the inventors also contemplate a method of analyzing genomic sequence data in which a BAM server receives a plurality of genomic sequence reads, wherein the plurality of genomic sequence reads are obtained from a genome of a tumor sample and a genome of a normal sample of a patient. The BAM server then processes the genomic sequence reads to produce a plurality of differential sequence objects that comprise a copy number and an allele fraction for an allele within the tumor genome. An analytics engine (that is coupled to the BAM server) then processes the copy number and the allele fraction for the allele to so determine an allelic state for the allele.

In a typical embodiment of such methods, a differential sequence database is coupled to the BAM server and the analytics engine such that the BAM server provides the differential sequence object to the differential sequence database and such that the differential sequence database provides the differential sequence object to the analytics engine. Furthermore, it is contemplated that a graphic output is generated by the analysis engine that plots the allelic state for the allele in an allelic state diagram.

In a further contemplated aspect of the inventive subject matter, a method of ex-vivo characterizing genomic information from a tumor includes a step of determining an allelic state for an allele in the tumor genome, and a further step of using the determined allelic state to identify the tumor as being a monoclonal tumor or as comprising at least two distinct tumor clones.

In such methods, it is further contemplated to use the determined allelic state to identify a relationship of the tumor clones (e.g., as being distinct and unrelated or as being related). Where the clones a related, it is contemplated that the determined allelic state can be employed to identify a clonal history for the distinct tumor clones.

Thus, the inventors also contemplate a method of ex-vivo characterizing a tumor clone in a tumor mass in which in one step genomic sequence information from the tumor mass is obtained (e.g., from a BAM server). In another step, the genomic information is used to determine an allelic state for an allele in the tumor genomic sequence information. In a further step, the location of the allelic state for the allele in an allele state diagram is determined (e.g., in a graphic display or in silico, or numerically), and the location is used to identify the clone as monoclonal or polyclonal. For example, a clone is monoclonal when the location of the allelic state is on a vertex of the allelic state diagram.

In yet another aspect of the inventive subject matter, the inventors contemplated a method of providing treatment information for treatment of a tumor. In such method, allelic state information for the tumor is ascertained, and presence or emergence of (a) a clone or (b) an evolutionary pattern of clones is ascertained within the tumor that is indicative of at least one of susceptibility of the tumor to treatment with a drug, and an increased risk of drug resistance or metastatic potential. Most typically, the step of identifying presence or emergence is based on prior treatment data or a priori known data.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIGS. 3A-3D depict an exemplary set of allelic state diagrams for the simulated monoclonal tumor genome of FIG. 2 with different levels of normal contaminant: FIG. 3A illustrates 0% normal contaminant, FIG. 3B illustrates 10% normal contaminant, FIG. 3C illustrates 50% normal contaminant, and FIG. 3D illustrates 90% normal contaminant, indicating the difference is resolution as a function of level of normal contamination.

FIGS. 7A and 7B are exemplary illustrations of allelic state diagrams for two glioblastoma multiforme (GBM) tumors: GBM-06-0145 (FIG. 7A) and GBM-06-0185 (FIG. 7B). The fitted parameters found normal contamination at 21.5% and 14.6%, respectively. FIG. 7A depicts only clonal allelic states and no evidence of transitional allelic states, indicating that GBM-06-0145 is a monoclonal tumor, while FIG. 7B depicts both clonal states and multiple transitional allelic states. Since the transitional allelic states (marked with (*)) feature three different mixture percentages, this polyclonal tumor must consist of at least three sub-clones.

The black X's plotted in FIG. 7B represent "landmark" allelic states suitable for use to determine the clonal mixture of GBM-06-0185.

FIGS. 7C and 7D are exemplary illustrations of allelic state diagrams for two lung squamous cell carcinoma (LUSC) tumor: LUSC-34-2596 (FIG.7C) and LUSC-66-2756 (FIG. 7D).

Figure 8:
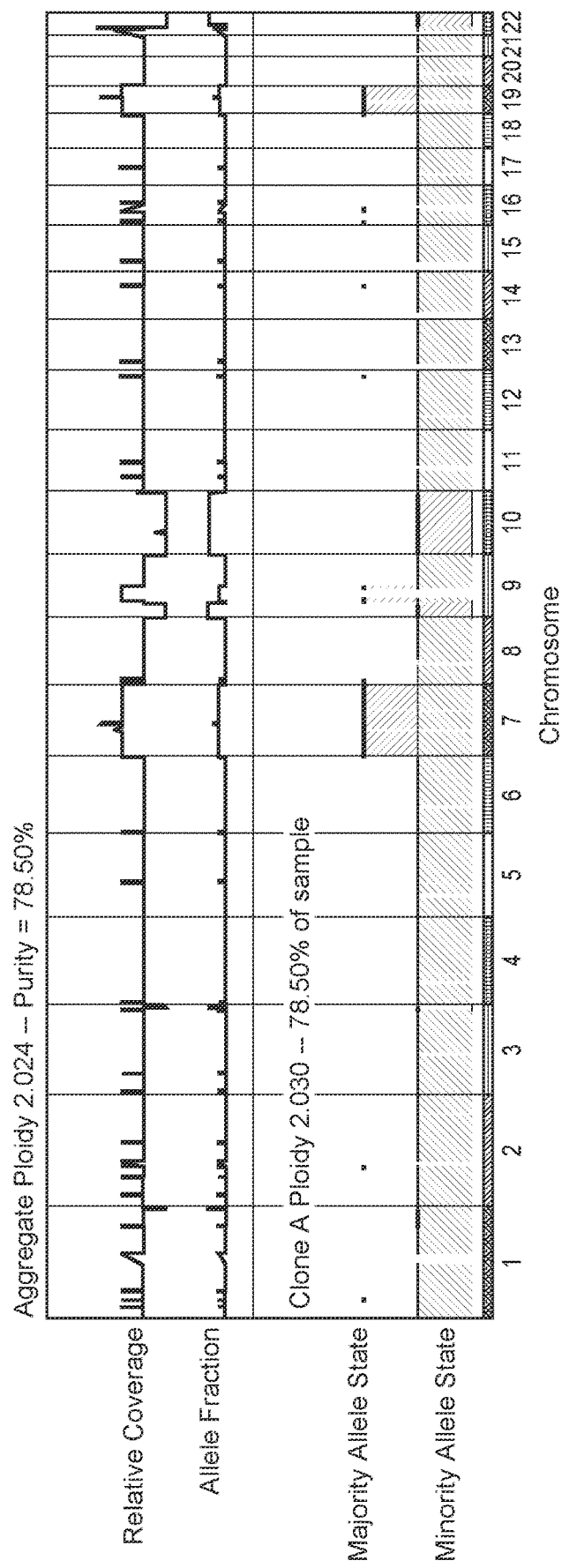

FIG. 8 is an exemplary plot depicting the monoclonal karyotype for GBM-06-0145. The "Relative Coverage" and "Allele Fraction" displayed at the top of the plot shows both the observed results output by BamBam and the computed coverage and allele fraction generated by modeling the mixture of the single clone and normal contamination. The comparison of real versus modeled data shows very strong agreement. The clone's karyotype below shows the majority and minority allelic states for the tumor genome, showing amplification of one copy of entire chr7 and chr19, complete loss of one copy of chr10, and arm-level loss of chr9p.

Figure 9:
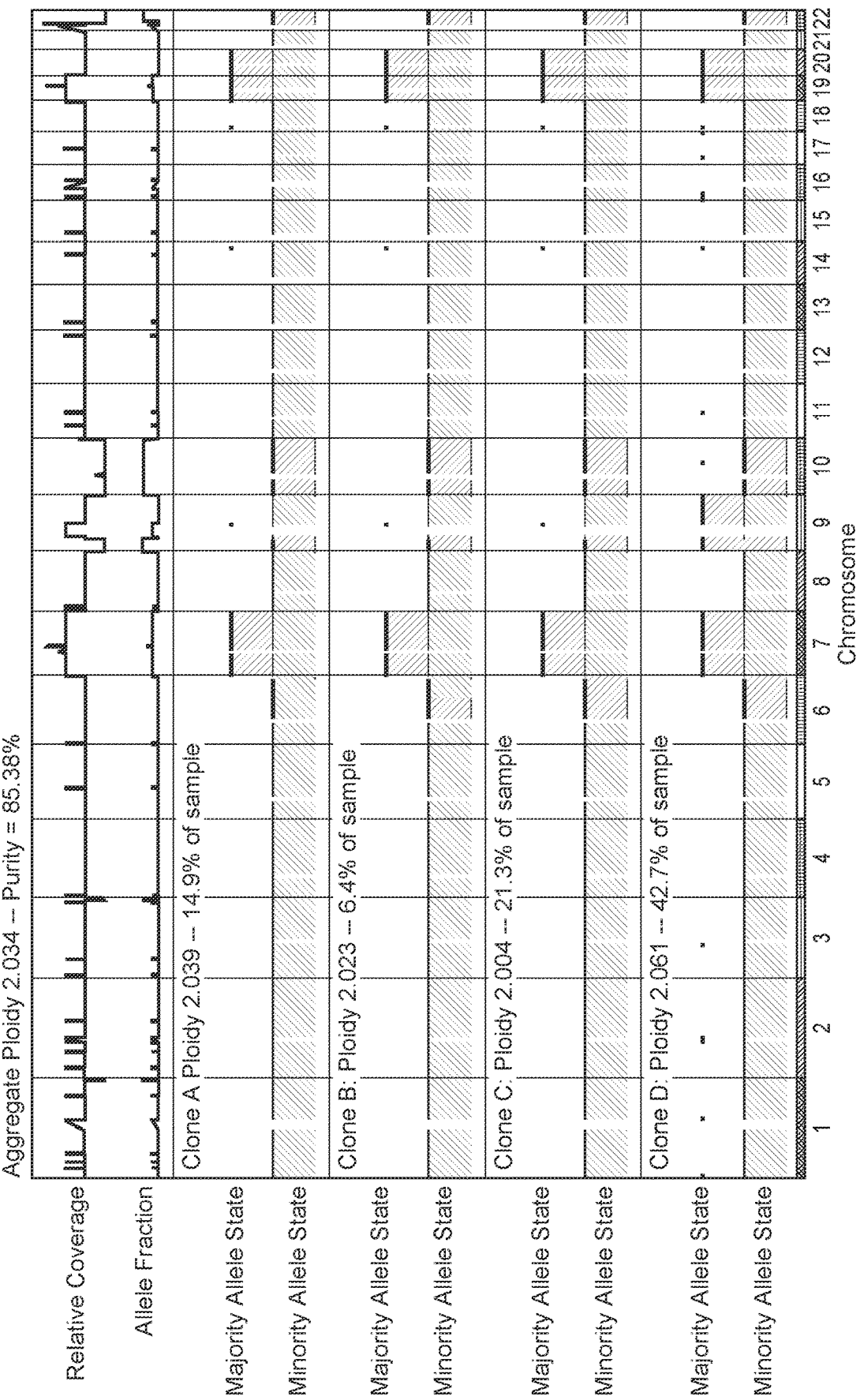

FIG. 9 is an exemplary plot depicting the polyclonal karyotypes for GBM-06-0185. A total of 4 distinct clones were identified in this tumor, with clone D determined to be the dominant clone of the population, comprising 42.7% of the tumor sample. All clones have single-copy amplifications of chr7, chr19 & chr20, single copy loss of chr10 and chr22, and loss of chr9p in common. Clones B, C, & D all have deletions in chr6, but clone B's deletions are focal while clones C & D display arm-level loss of chr6q. Clone D is further distinguished by amplification of the intact copy of chr9.

Figure 10:
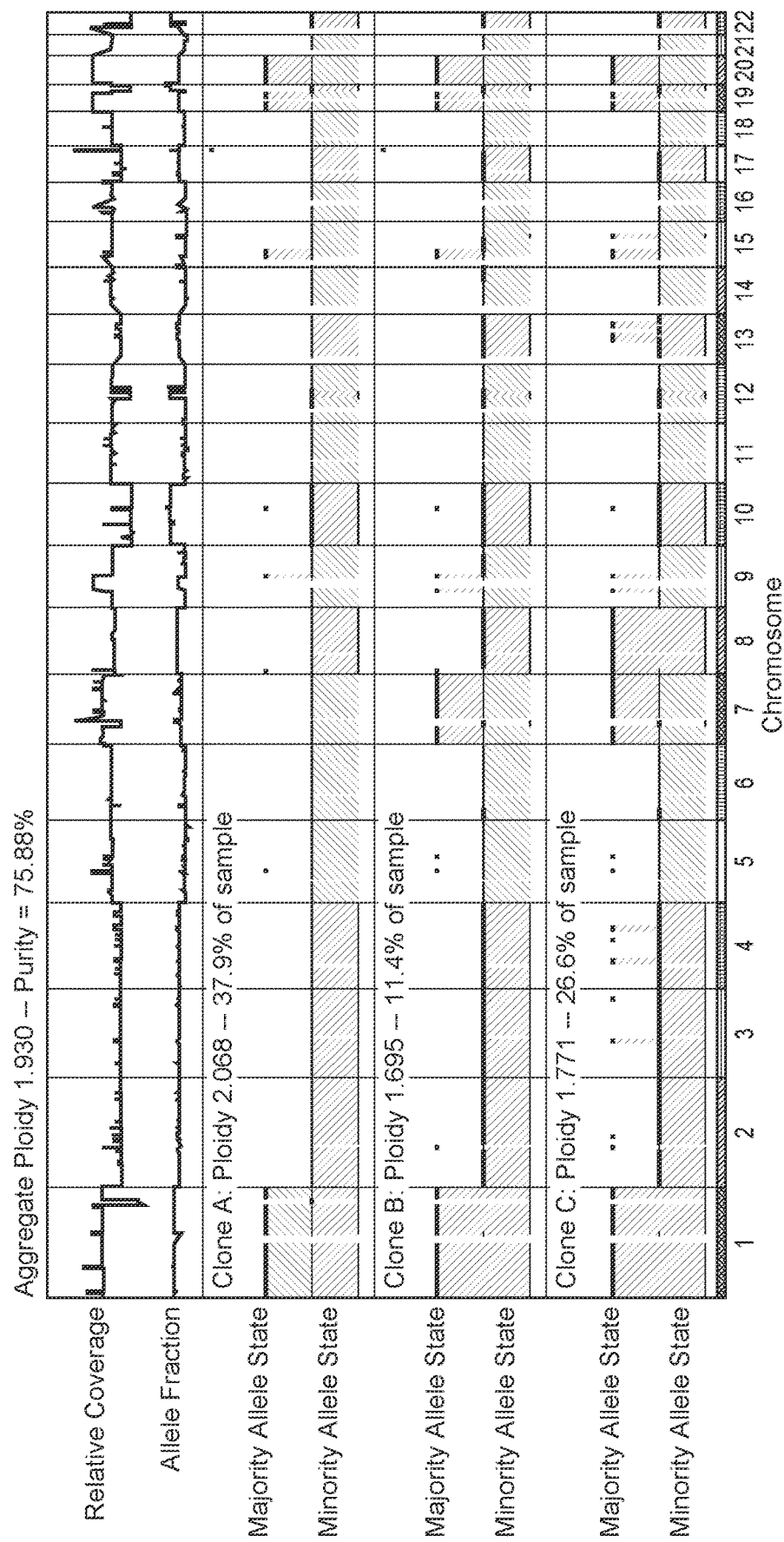

FIG. 10 is an exemplary plot depicting the polyclonal karyotypes for GBM-06-0152. Three clones were identified in this tumor sample that has an estimated 24.1% normal contamination. All clones share amplifications of chr1, chr19 & chr20, deletions of chr10 & chr22, and focal losses of chr12 related to the chromothripsis-like event that created two DMs described in the previous chapter. Clones B & C exhibit amplification of chr7 and deletions of the nonamplified copy of chr1 as well as chr2, chr3, chr4, chr8, chr13, and chr17. Clone C further amplifies the remaining copy of chr8.

Figure 11:
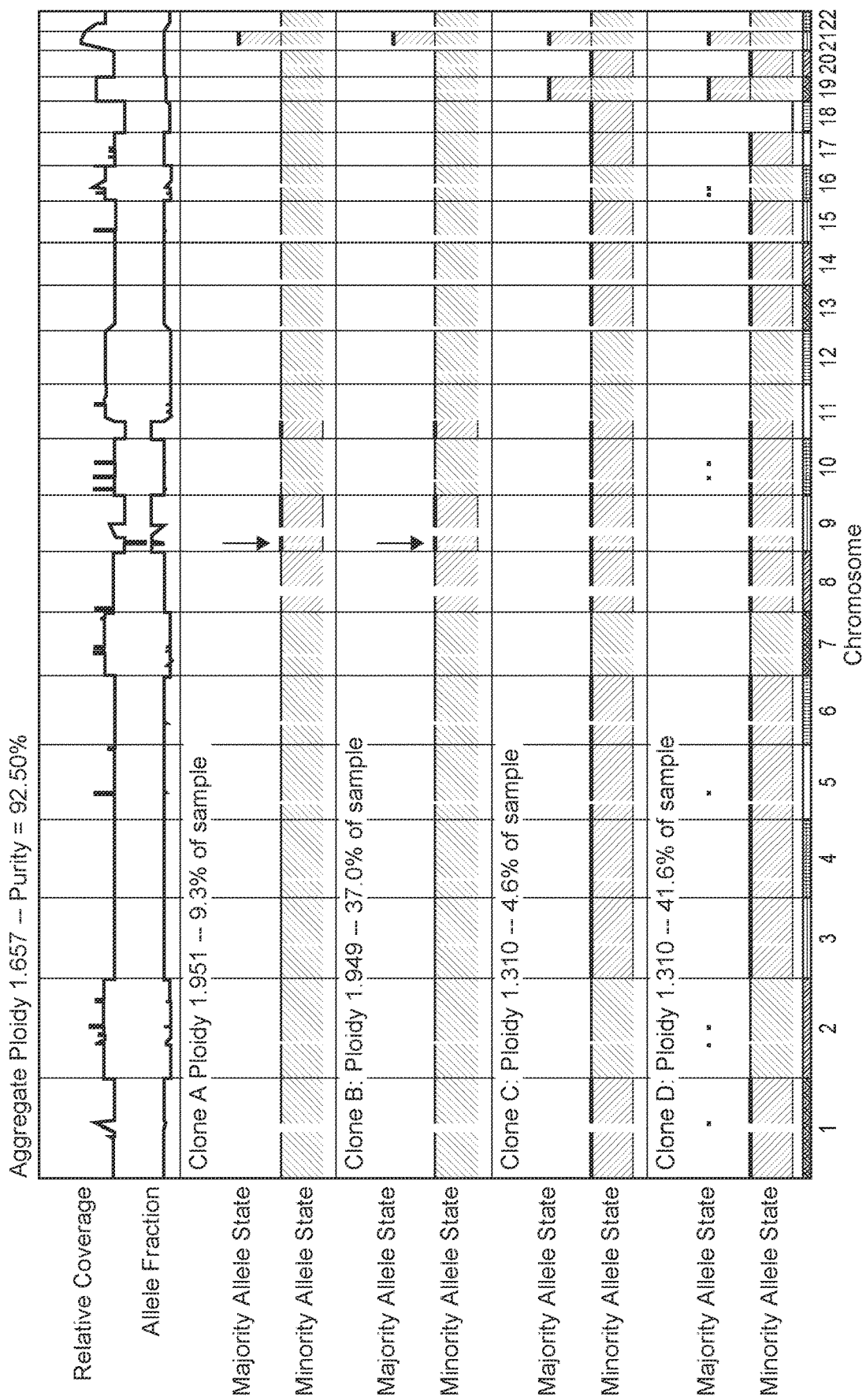

FIG. 11 is an exemplary plot depicting the polyclonal karyotypes for GBM-06-1086. Four clones were identified in this tumor sample that has an estimated 7.5% normal contamination. All clones share amplification of chr21 and deletions of chr9 & chr11p. Clones C & D exhibit significant chromosomal loss, deleting chr1, chr3, chr4, chr5, chr6, chr8, chr10, chr13, chr14, chr15, chr17, chr18, and chr20. The dominant clone D, making up 41.6% of the tumor sample, further deletes the sole remaining copy of chr18 and amplifies chr19. The black arrows indicate the position of CDK2NA in clones A & B, highlighting the arrival of the focal deletion of CDKN2A in the latter clone.

Figure 12:
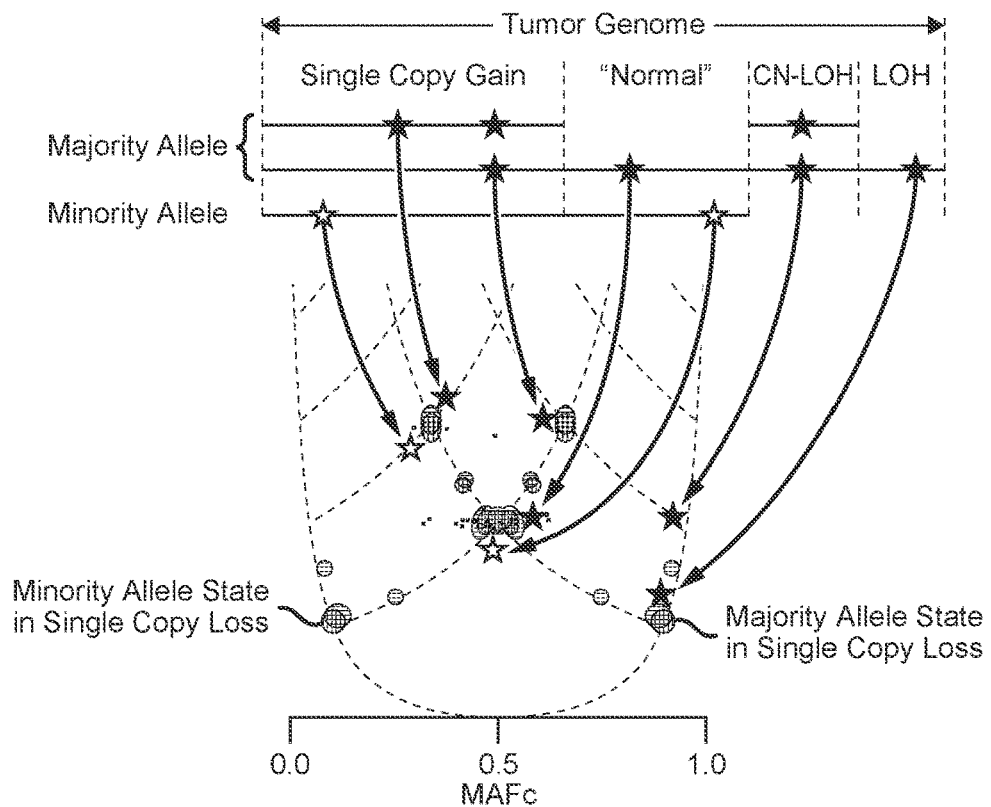

FIG. 12 is an exemplary illustration of phased mutations on the dual ASD. A representative region on the tumor genome is shown, consisting of a region in the single copy gain allelic state, a region in the "normal" allelic state, a region exhibiting copy-neutral loss of heterozygosity (CN-LOH), and a region exhibiting LOH. Three mutations are found in the amplified region, two majority-phased (red stars) and one minority-phased (blue star). Two mutations are found on the "normal" allelic state, one majority-phased and another minority-phased. Both regions exhibiting LOH have one mutation each phased to the sole remaining allele, and are thus majority-phased. The dual ASD below shows where each of these mutations would be found, using each mutation's corrected allele fraction, MAFc, to determine its location along the x-axis. Note the different placement of the two majority-phased mutations in the single-copy gain allelic state, where only the mutant allele that exists on both majority alleles (i.e. mutated before amplification) is found near the single copy gain majority allelic state. The other is found near the single copy gain minority allelic state, correctly identifying that the mutation exist on only one copy of the majority allele. Finally, note that the minority-phased mutations in blue are all found towards the left-half of the dual ASD.

Figure 13:
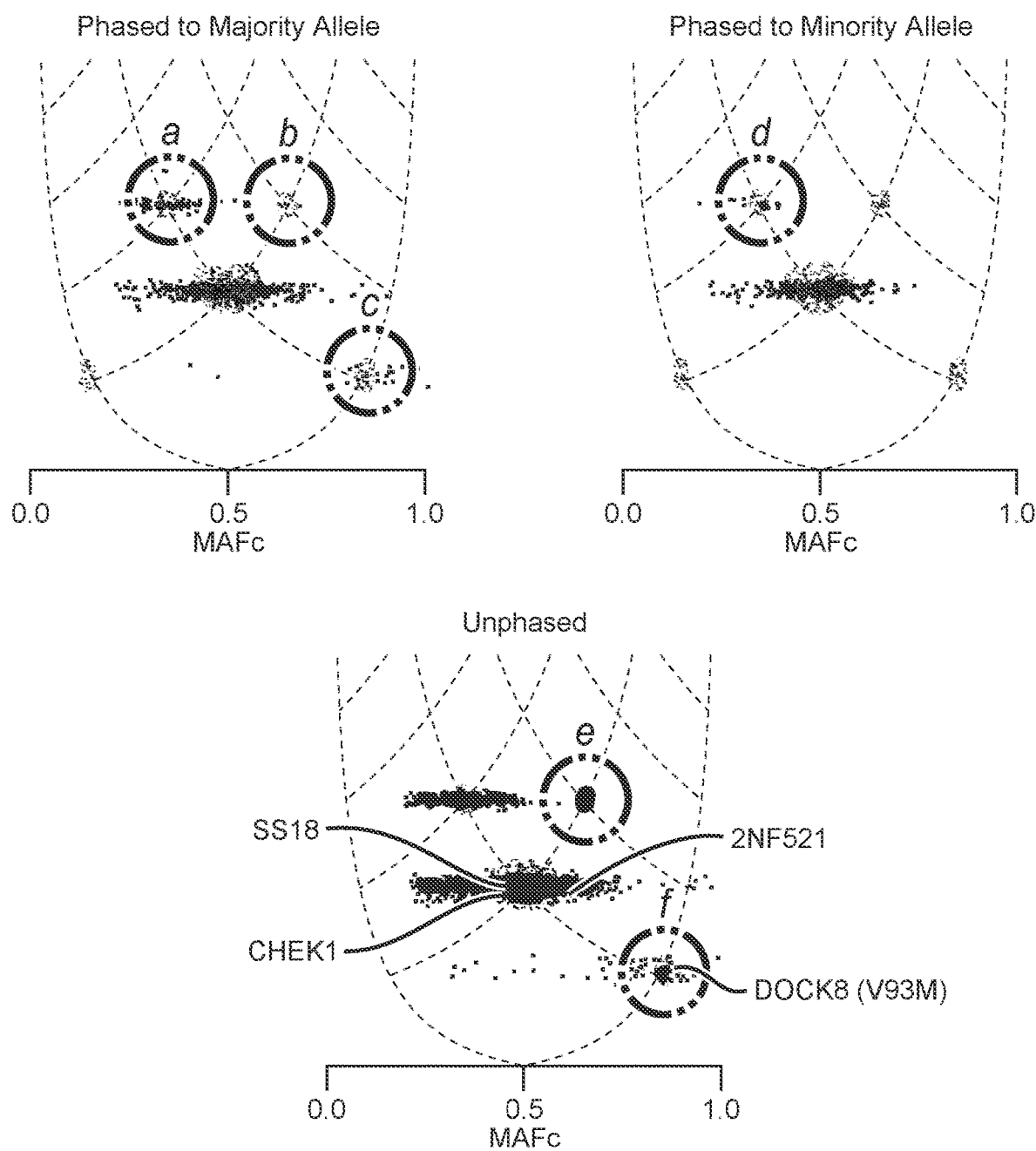
Figure 14:
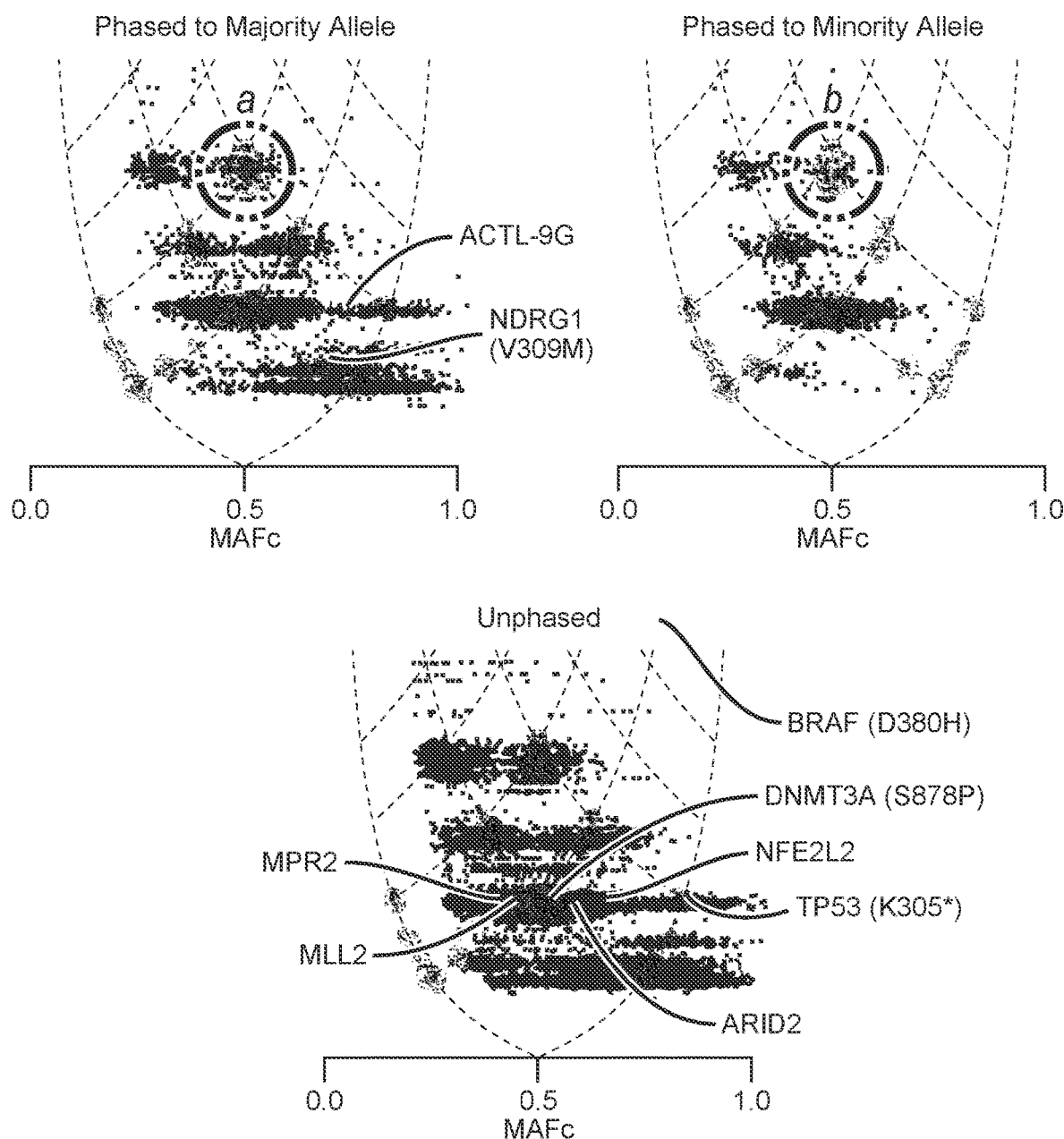

FIG. 13 is an illustration of phased mutations on the dual ASD for tumor GBM-06-0145. 7 regions are encircled on these plots: (a) majority-phased to an amplified allelic state yet presents with MAFc suggesting the mutation is only on one of the two copies, (b) majority-phased to an amplified allelic state with MAFc suggesting mutation is present on both amplified copies, (c) majority-phased with allele fraction consistent with the LOH allelic state, (d) minority-phased in the majority-amplified allelic state with MAFc consistent with single copy, (e) unphased mutations with MAFc consistent with amplified allelic state, and (f) unphased mutations with MAFc consistent with LOH allelic state FIG. 14 is an illustration of phased mutations on the dual ASD for tumor LUSC-34-2596. The two encircled regions, (a) and (b), show a number of mutations phased to the majority and minority alleles, respectively, in the balanced amplified allelic state (2,2). One majority-phased mutation in NDRG1 is found in a transitional allelic state with matching MAFc. The locations of two missense mutations, in BRAF & DNMT3A, and one nonsense mutation in TP53 are shown in the unphased plot, placing BRAF in a highly amplified allelic state, DNMT3A in the "normal" allelic state, and TP53 in the CN-LOH state.

DETAILED DESCRIPTION

The inventors have discovered that clonality of a genetically heterogeneous sample can be readily resolved using an approach that uses an allelic state model (e.g., expressed as allelic state diagram), and that the so obtained clonality information can be used for various purposes, including analytic, prognostic, and diagnostic uses.

For example, the methods and systems contemplated herein provide the ability to computationally dissect a tumor's population using whole genome sequencing data, and where desired, to visually assess a tumor sample's clonality using an allelic state diagram. Viewed from a different perspective, the clonal mixture of a tumor can now be determined by decomposition of the tumor population into the major clones of the tumor cell population and by estimation of normal contamination to account for the copy number and allele fraction (which is preferably performed using BamBam, as described in WO2013/074058). Still further, contemplated systems and methods all for a determination and phasing of whole genome karyotypes of all major clones, which in turn allows inferring the phylogenetic tree of polyclonal tumor genomes to time the emergence of clone-specific copy number alterations. Finally, by using phasing and mutant allele fraction, emergence of mutations can be timed with respect to their encompassing copy number alterations.

Therefore, in one aspect of the inventive subject matter, it should be appreciated that clonality and timing information will help better understand the dynamic nature of individual tumors, which may be reflective of a tumor type, or an individual's or tissue's response to the presence or development of the tumor. Remarkably, all of this information can be discovered from just a single tumor biopsy, making contemplated systems and methods particularly useful in an ex vivo diagnostic approach.

In another aspect of the inventive subject matter, it should be appreciated that the phylogenetic-based mutation models contemplated herein can be employed to analyze the mutations of related samples (e.g., primary tumor and its metastases) to so reconstruct the mutational history of a cancer as it spread. The ability to determine a tumor's clonality and identify all of the major clones that comprise the growing tumor mass, all from the whole genome sequencing data of a single biopsy, opens up a wide variety of potential clinical applications. For example, in a scenario where a newly-diagnosed patient's tumor is biopsied and all of the major clones are identified via clonal analysis. A clinician could then use this clonality analysis to tailor the patient's treatment according to the alterations specific to the clone furthest up the evolutionary tree, the progenitor tumor cell, with the hope that treating the initial tumor mass, derivative clones will also be targeted. On the other hand, in a scenario where a patient is diagnosed with a slow-growing tumor that can be safely monitored for a longer period of time before surgery or the beginning of chemotherapy, clonal analysis of a series of biopsies could be performed and, by tracking the clonal composition of the tumor through time, a clinician can identify the clones that are growing most rapidly. By designing a treatment that targets not what is currently the dominant clone, but the clone that is set to become the dominant clone, might more effectively treat the cancer.

Clonality analysis is also contemplated to prove useful in better understanding the metastatic spread of cancers. In such scenario, clonal analysis of a primary tumor and a series of metastases is used to determine all of the major clones present in the spreading tumor. By inspecting the clonal composition of the primary and each metastasis, one can determine how each clone spreads and discover if one or more particular clones exist that show increased metastatic potential. By determination of the characteristics unique to the metastatic clones, the inventors contemplate that identification of emergence of these characteristics in minor clones of another patient's primary tumor an "early warning" signal may be developed for determination of likelihood of imminent metastasis.

With respect to methods of data acquisition for clonality analysis, it is preferred that genomic analysis to identify copy number and allele fractions are determined using systems and methods in which multiple relatively small genomic sequence sub-strings (e.g., short reads from sequencing runs) of respective larger genetic sequence strings from a first and second tissue sample (e.g., healthy and diseased tissue) are obtained. The genetic sequence strings are then incrementally synchronized using one or more known positions of at least one of corresponding sub-strings to so produce a local alignment. The so generated local alignment is then analyzed (typically using a reference genomic sequence) to generate a local differential string between the first and second sequence strings within the local alignment that thus contains significant differential information (typically relative to the reference genomic sequence). A differential genetic sequence object for a portion or even the entire genome is then created using the local differential string, and most typically a plurality of local differential strings. It should be noted that incremental synchronization to produce local alignments and differential information provides various technical advantages, including a significant increase in processing speed of an entire genome, as well as the capability to produce allele specific information (e.g., copy number, allele fraction, etc.)

In such systems and methods, it should be appreciated that instead of processing two extremely large files to generate another extremely large intermediate (or even output) file, genome wide analysis can be achieved in multiple significantly smaller portions wherein the smaller portions are aligned to a reference genome using known positions within the genome of one or more sub-strings. Viewed from another perspective, alignment is performed by incremental synchronization of sequence strings using known positions of substrings and a reference genome sequence, and an output file can be generated that comprises only relevant changes with respect to a reference genome. Thus, the processing speed is significantly improved and the amount of data required for production of a meaningful output is dramatically reduced. Still further, it should be noted that such systems and methods allow, inter alia, haplotyping/somatic and germline variant calling, and determination of allele-specific copy numbers. Moreover, the systems and methods presented herein are suitable for use with sequence information in SAM/BAM-format.

For example, multiple sequencing fragments (e.g., short reads from a tumor sample of a donor and corresponding non-tumor sample of the same donor) are aligned to the same reference genome, which is employed to organize the sequencing fragments from the samples. Thus, such methods use two sequencing fragment datasets (one from the tumor, the other from corresponding normal "germline" tissue) from the same patient and the reference genome, and reads the datasets such that all sequences in both datasets overlapping the same genomic position (based on the reference genome and annotation in sub-strings) are processed at the same time. This is the most efficient method for processing such data, while also enabling complex analyses that would be difficult or impossible to accomplish in a serialized manner, where each dataset is processed by itself, and results are only merged afterwards. A particular suitable system is described in WO2013/074058, incorporated by reference herein.

With the release of multiple fully-sequenced tumor and matched normal genomes from projects like The Cancer Genome Atlas (TCGA), there is great need for tools that can efficiently analyze these enormous datasets.

To this end, we developed BamBam, a tool that simultaneously analyzes each genomic position from a patient's tumor and germline genomes using the aligned short-read data contained in SAME AM-formatted files (SAMtools library; Li H, Handsaker B, Wysoker A, Fennell T, Ruan J, Homer N, Marth G, Abecasis G, Durbin R; 1000 Genome Project Data Processing Subgroup. The Sequence Alignment/Map format and SAMtools. Bioinformatics. 2009 Aug 15; 25(16):2078-9. Epub 2009 Jun 8). BamBam interfaces with the SAMtools library to simultaneously analyze a patient's tumor and germline genomes using short-read alignments from SAM/BAM-formatted files. In the present disclosure the BamBam tool can be a sequence analysis engine that is used to compare sequences, the sequences comprising strings of information. In one embodiment, the strings of information comprise biological information, for example, a polynucleotide sequence or a polypeptide sequence. In another embodiment, the biological information can comprise expression data, for example relative concentration levels of mRNA transcripts or rRNA or tRNA or peptide or polypeptide or protein. In another embodiment, the biological information can be relative amounts of protein modification, such as for example, but not limited to, phosphorylation, sulphation, actylation, methylation, glycosilation, sialation, modification with glycosylphosphatidylinositol, or modification with proteoglycan.

This method of processing enables BamBam to efficiently calculate overall copy number and infer regions of structural variation (for example, chromosomal translocations) in both tumor and germline genomes; to efficiently calculate overall and allele-specific copy number; infer regions exhibiting loss of heterozygosity (LOH); and discover both somatic and germline sequence variants (for example, point mutations) and structural rearrangements (for example, chromosomal fusions. Furthermore, by comparing the two genome sequences at the same time, BamBam can also immediately distinguish somatic from germline sequence variants, calculate allele-specific copy number alterations in the tumor genome, and phase germline haplotypes across chromosomal regions where the allelic proportion has shifted in the tumor genome. By bringing together all of these analyses into a single tool, researchers can use BamBam to discover many types of genomic alterations that occurred within a patient's tumor genome, often to specific gene alleles, that help to identify potential drivers of tumorigenesis.

To determine if a variant discovered is somatic (that is, a variant sequence found only in the tumor) or a germline (that is, a variant sequence that is inherited or heritable) variant requires that we compare the tumor and matched normal genomes in some way. This can be done sequentially, by summarizing data at every genomic position for both tumor and germline and then combining the results for analysis. Unfortunately, because whole-genome BAM files are hundreds of gigabytes in their compressed form (1-2 terabytes uncompressed), the intermediate results that would need to be stored for later analysis will be extremely large and slow to merge and analyze.

To avoid this issue, BamBam reads from two files at the same time, constantly keeping each BAM file in synchrony with the other and piling up the genomic reads that overlap every common genomic location between the two files. For each pair of pileups, BamBam runs a series of analyses listed above before discarding the pileups and moving to the next common genomic location. By processing these massive BAM files with this method, the computer's RAM usage is minimal and processing speed is limited primarily by the speed that the file system can read the two files. This enables BamBam to process massive amounts of data quickly, while being flexible enough to run on a single computer or across a computer cluster. Another important benefit to processing these files with BamBam is that its output is fairly minimal, consisting only of the important differences found in each file. This produces what is essentially a whole-genome diff between the patient's tumor and germline genomes, requiring much less disk storage than it would take if all genome information was stored for each file separately.

BamBam is a computationally efficient method for surveying large sequencing datasets to produce a set of high-quality genomic events that occur within each tumor relative to its germline. These results provide a glimpse into the chromosomal dynamics of tumors, improving our understanding of tumors' final states and the events that led to them.

BamBam enables a rapid comparison of tumor (somatic) and germline matched sequencing datasets. The results output by BamBam are varied, producing an exhaustive catalogue of the somatic and germline variants contained by each patient's samples. This catalogue provides researchers with the ability to quickly find important changes that occurred during the tumor's development, but also provide high-quality variants present in the patient's germline that may indicate predisposition to disease. Further improvements of BamBam will consist of methods that specifically search for multiple types of variants occurring in the same genomic region (for example, one allele of a gene deleted, the other allele containing a truncating mutation by breakpoint) that may point to drivers of tumorigenesis. We also plan to extend BamBam's ability to processing more than pairs of genomes, as well as provide researchers with the ability to plug in their own analysis methods into BamBam's pipeline.

In additional embodiments, the polynucleotide nucleic acids may be used in any molecular biology techniques that have yet to be developed, provided the new techniques rely on properties of nucleic acid molecules that are currently known, including, but not limited to, such properties as the triplet genetic code and specific base pair interactions.

In a genetic sequence analysis ecosystem, which includes sequence analysis engine coupled with one or more databases, possibly over network (for example, LAN, WAN, VPN, Internet, etc.). Preferred databases include genetic database storing genetic sequence strings for one or more tissues, differential sequence database storing differential genetic sequence objects representing local differential strings, and medical records database storing one or more medical records associated with a patient, person, population, or other type of entities. Medical records database can also store one or more differential genetic sequence objects, possibly associated with patients, persons, populations or other groups.

One aspect of the inventive subject matter is considered to include management of differential genetic sequence objects. Through analysis of genetic sequence strings, analysis engine can create differential strings or constellations of differential strings. Differential strings can be converted to differential genetic sequence objects, which in turn can be stored in differential sequence database or medical records database. The sequence objects can be tagged with one or more attributes describing the nature of the objects. Example attributes can include time stamps of object creation, time stamp of when sample was taken from a patient, patient name, demographic information, tissue type (for example, healthy, diseased, tumor, organ tissue, etc.), or other features. The attributes can by leveraged by analysis engine to establish one or more correlations among characteristics associated with medical records in medical records database.

Management of differential genetic sequence objects covers a broad spectrum of roles or responsibilities. As discussed above, one aspect includes creation of such objects. Analysis engine is also preferably configured to update, analyze, modify, track in time, delete, copy, split, append, or otherwise manipulate the sequence objects as desired. Further, analysis engine can provide a differential genetic sequence object management interface, possibly on output device. For example, in some embodiments, ecosystem operates as a for-fee service comprising one or more web servers available over the Internet. In such an embodiment, a computer with a browser can interface with analysis engine to manage or interact with the differential genetic sequence objects.

In some embodiments, as discussed further below, analysis engine is configured to analyze genetic sequence strings obtained from genetic database. Preferably the genetic sequence strings are associated within at least two different tissue samples. Analysis engine produces one or more local alignments by incrementally synchronizing at least two sequences using at least a known position of corresponding sub-strings in the sequence strings. Further, analysis engine uses the local alignment to generate one or more local differential strings or constellations of differential strings between the genetic sequence strings. Analysis engine can then use the differential strings to update differential genetic sequence objects in differential sequence database or medical records database. The differential sequence objects can then be used for further analysis.

In some embodiments, analysis engine communicatively couples with medical records database that stores differential genetic sequence objects for specific patients, persons, individuals, families, populations, or other groups. Analysis engine obtains a differential sequence object for a patient and produces a patient specific data set based on presence of a local differential string or constellation of differential string associated with the patient's sequence object. Then, analysis engine can leverage the patient-specific data set to generate or otherwise produce one or more patient specific instructions. For example, through analysis of the patient's specific local differential strings, analysis engine can determine if there is a correlation between the patient's specific differential strings and known conditions, which in turn can be mapped to instructions. Contemplated instructions can include a diagnosis, a prognosis, a recommended treatment, a prediction, a prescription, or other type of instructions.

In yet other embodiments, analysis engine obtains differential genetic sequence objects stored in medical records database where the sequence objects are associated with a population of individuals. The analysis engine identifies a constellation of local differential strings from multiple sequence objects and generates constellation record from the constellation. Constellation record comprises a representation of information (for example, attributes, properties, metadata, characteristics, etc.) related to local differential strings associated with the population Analysis engine uses constellation records to generated population analysis record. Thus, the differential genetic sequence objects can be mapped to population segments.

Still another embodiment includes analysis engine using the differential genetic sequence object to determine an extent that a person's genetic sequence deviates from a reference sample. A reference differential genetic sequence object, possibly representing a real person or a canonical person, can be stored as a medical record in medical records database. Analysis engine calculates a deviation between a person's local differential strings from different sequence objects associated with the person and the local differential strings from the reference differential genetic sequence object. Once the deviation is calculated, analysis engine generates a deviation record representing the deviation or departure. Similar to other records in the system, deviation record can also include attributes reflecting the characteristics of the information in the record (for example, person name, time stamps, sample types, etc.). Analysis engine can then leverage deviation record to generate person-specific deviation profile indicating how or to what degree the person genetic sequences deviate from the reference differential stings.

Regardless of the type of analysis or result generated (for example, patient instructions, population analysis, person-specific profile, etc.), analysis engine can further configuration output device to present the result. Output device preferably comprises a computing device coupled with analysis engine, possibly over network. Examples of output device include cell phones, information kiosks, computer terminals at point of care, insurance company computers, printers, imaging devices, genomic browsers, or other types of devices.

Using a system according to the inventive subject matter will therefore typically include a genetic database. As already noted above, it should be appreciated that the genetic database may be physically located on a single computer, however, distributed databases are also deemed suitable for use herein. Moreover, it should also be appreciated that the particular format of the database is not limiting to the inventive subject matter so long as such database is capable of storing and retrieval of first and second genetic sequence strings representing respective first and second tissues, wherein the first and second sequence strings have a plurality of corresponding sub-strings.

Likewise, it should be noted that the particular format of the first and second genetic sequence strings is not limiting to the inventive subject matter so long as first and second genetic sequence strings will include one or more corresponding sub-strings for which the location in a genome is known. Therefore, suitable data formats will include simple ASCII or binary code, and the sequence strings may be formatted following specifications commonly employed in currently known sequence analytic tools. Therefore, especially preferred formats include EMBL, GCG, fasta, SwissProt, GenBank, PIR, ABI, and SAM/BAM format.

Depending on the particular nature of analysis and samples, the type of genetic sequence strings may vary considerably, and it should be pointed out that the sequences may be nucleic acid sequences (DNA or RNA) as well as protein sequences. Most typically, however, the genetic sequence strings will be nucleic acid strings that will represent significant portions of the genome, transcriptome, and/or proteome of the first and second tissues under analysis. For example, it is contemplated that the first and second genetic sequence strings represent at least 10%, more typically at least 25%, more typically at least 50%, even more typically at least 70%, and most typically at least 90% or even substantially the entire (at least 98%) genome, transcriptome, or proteome of the first and second tissues. Thus, it should be appreciated that the systems and methods presented herein will allow for a rapid and highly comprehensive overview of significant differences between first and second tissues while producing a compact and informative output file.

Depending on the type of tissue under investigation, it should be noted that multiple types of analyses can be performed. For example, where the first and second tissues originate from the same biological entity, healthy tissue may be compared against a different healthy tissue or healthy tissue may be compared against a corresponding diseased tissue (for example, tumor tissue). Thus, the biological entity may be a healthy individual or an individual diagnosed with a disease or disorder. On the other hand, where first and second tissues are derived from a cell line (immortalized or primary), genetic effects or epigenetic effects of drugs may be rapidly identified. Similarly, where the first and second tissues are derived from a stem cell, changes in genetic composition or genetic plasticity of the developing embryo may be analyzed. In still further contemplated examples, the first and second tissue may be of an experimental animal model to investigate progression of a disease or effect of a treatment. Alternatively, first and second tissue may even be from a yeast, recombinant bacterial cell, and/or a virus.

Consequently, it should be recognized that the nature of the corresponding sub-strings will vary considerably and will at least in part depend on the type of tissue sampled and on the amount of genomic coverage. However, it is typically preferred that the genomic coverage is relatively high and that in most cases the entire genome is analyzed. Thus, corresponding sub-strings will typically include homozygous and heterozygous alleles.

Regardless of the type of sub-strings, it is generally preferred synchronizing will include a step of aligning at least one of the plurality of sub-strings based on an a priori known location within the first string. As numerous genomes for various organisms (and especially human) are already substantially completely annotated and as even unknown sequences are often annotated with at least a putative function, and as substantially the (linear) sequence entire genomes are known, the number of priori known locations with respect to a reference genome is high. Thus, knowledge of annotations within the reference genome will serve as a roadmap for effective and accurate synchronization. Of course, it should be appreciated that the nature of the reference genome is not necessarily limited to a genome of a single healthy tissue, but that the reference genome may be any defined (actual or calculated) genomic structure. For example, the reference genome may be constructed from a (typically single tissue of a) plurality of healthy individuals to so generate a consensus reference sequence. Alternatively, the reference string may be based on a consensus of multiple tissues of the same (or different) individual, or on a consensus of diseased tissue samples (from the same or multiple patient).

Consequently, it should be recognized that the differential genetic sequence object will provide information of one or more sample tissue(s) relative to a reference tissue. Thus, and depending on the choice of the reference string, the information content for the differential genetic sequence object may vary considerably. For example, the differential genetic sequence object may provide information that the sample is a match for a particular subpopulation (as defined by the reference string) or that the sample has a plurality of mis-matches that may or may not be associated with a disease or condition.

In further preferred aspects of the inventive subject matter, the synchronization may also be performed by aligning the sub-string(s) within a window having a length of less than a length of the at least one of the plurality of sub-strings. Most preferably, synchronization is performed by iteratively and incrementally synchronizing the first and second sequence strings throughout the entire length of the first sequence string. Viewed from a different perspective, synchronizing will thus be performed in a manner similar than that of a zipper in which the two halves are incrementally matched up to produce an alignment. Using the same image, only mis-matched portions of the closed zipper are then reflected in the differential genetic sequence object.

Consequently, it should thus be recognized that the differential genetic sequence object will represent one or more local differential strings, typically at least for a defined portion of the genome (for example, at least one chromosome), and more typically for substantially the entire genome of the first or second tissue. Of course, it should be noted that based on the already known position and/or determined deviation from the reference string, the differential genetic sequence object will typically include one or more attributes with metadata describing the differential genetic sequence object. For example, the attribute may be descriptive of a state of the first and/or second tissues. Where the state is a physiological state, the metadata may reflect neoplastic growth, apoptosis, state of differentiation, tissue age, and/or responsiveness to treatment for the tissue. On the other hand, where the state is a genetic status, the metadata may reflect ploidy, gene copy number, repeat copy number, inversion, deletion, insertion of viral genes, somatic mutation, germline mutation, structural rearrangement, transposition, and/or loss of heterozygosity. Similarly, the state may include pathway model information that is associated with a signaling pathway within the tissues (for example, anticipated responsiveness to drugs, defects in receptors, etc.), and especially contemplated pathways include signaling pathways (for example, growth factor signaling pathway, transcription factor signaling pathway, apoptosis pathway, cell cycle pathway, hormone response pathway, etc.).

Output information provided by the systems and methods presented herein may be in form of a single differential genetic sequence object indicating multiple deviations from the reference string, or more than one differential genetic sequence object indicating individual deviations from the reference string, or any reasonable combination thereof. Most typically, the differential genetic sequence object will be in electronic format, and thus be retrieved and/or transferred as a computer readable file. As will be readily recognized the file is most preferably standardized, and it is especially preferred that the format conforms to a SAM/BAM format.

In light of the above, it should thus be appreciated that the differential genetic sequence object may be used in a variety of manners, and that the differential genetic sequence object is especially suitable for numerous applications in healthcare, population analysis, and personalized medicine.

For example, where one or more differential genetic sequence objects are known for an individual, a patient-specific data set may be produced that is based on a local differential string or on a constellation of multiple local differential strings in the differential genetic sequence object for the patient, and the patient-specific data set is then used to produce a patient-specific instruction. In a typical example, the inventors contemplate a method of providing a health care service in which an analysis engine is coupled to a medical records storage device that stores a differential genetic sequence object for a patient. The analysis engine will then generate patient-specific data using one or more local differential strings or a constellation of a plurality of local differential strings in the differential genetic sequence object for the patient, and produce a patient-specific instruction based on the patient-specific data set.

It should be appreciated that the medical records storage device may be configured in numerous manners and may be portable by the patient (for example, smart-card carried by the patient), accessible by the patient (for example, via smart phone), or remotely stored on a server that is accessible by the patient or medical professional of the patient. As can be taken from the discussion above, the differential genetic sequence object for the patient may include any number of local differential strings (i.e., sequence deviations at a specific position in the genome relative to a reference genome), and the local differential strings may be located in a defined area of the genome, on or more chromosomes, or even in throughout the entire genome. Similarly, the differential genetic sequence object may comprises multiple local differential strings that represent at least two tissue types (for example, healthy versus diseased), or at least two temporally spaced results for the same tissue (for example, prior to treatment with a particular drug at a particular regimen and after treatment commences).

Thus, and viewed from a different perspective, it should be noted that medically relevant information for the entire genome (or a fraction thereof [for example, chromosome or contiguous sequence stretch]) can be expressed as a deviation record having one or more local differential strings, and that the information can be used to compare against a database that contains treatment options, diagnoses, and/or prognoses associated with or for the local differential string. Where multiple local differential strings are present, it is noted that the combination of selected local differential strings may be indicative of a condition, predisposition, or disease, and that such constellation of multiple specific local differential strings may be used to generate the patient-specific data, which is then used to generate the patient-specific instruction. Thus, the nature of the patient-specific instruction will vary considerably, and may be a diagnosis, a prognosis, a prediction of treatment outcome, a recommendation for a treatment strategy, and/or a prescription.

In yet another preferred use of contemplated differential genetic sequence objects, the inventors discovered that genetic analysis is possible not only for individuals, but that also population-wide analyses can be conducted in a rapid and effective manner using the systems and methods presented herein. For example, in a method of analyzing a population, a plurality of differential genetic sequence objects (for example, for a plurality of individuals) are stored in a medical records database of a population, and an analysis engine will identify a constellation of a plurality of local differential strings (for example, based on polymorphisms, epigenetic changes, etc.) within the plurality of differential genetic sequence objects to produce a constellation record, which is then used to generate a population analysis record.

For example, the constellation record can be prepared for blood relatives, members of the same ethnic group or race, a population working in the same occupation, a population living in a selected geographic location. Alternatively, the population may also be defined by having members that share exposure to a pathogen or noxious agent, health history, treatment history, treatment success, gender, species, and/or age. Thus, it should be recognized that the constellation record is a genome-wide analytic tool that will allow identification of individuals as belonging to one or more specific groups as defined by the constellation record. Thus, the constellation record and associated methods may be useful to determine paternity or maternity or may be useful to generate a patient-specific record in view of the constellation record. For example, the patient-specific record may reveal predisposition to a disease or condition, or sensitivity to certain drugs or other agents. Consequently, the patient-specific record may present a risk assessment and/or an identification of the patient as belonging to a specified population. Alternatively, the patient-specific record may include a diagnosis, a prognosis, a prediction of treatment outcome, a recommendation for a treatment strategy, and/or a prescription that is typically at least in part based on a comparison of the constellation record of the patient with a population analysis record.

In a still further preferred use of contemplated differential genetic sequence objects, a reference differential genetic sequence object is generated (for example, as a consensus record as described above) and stored in a database. A deviation between a plurality of local differential strings in the differential genetic sequence object of a person and a plurality of local differential strings in the reference differential genetic sequence object is then determined to so produce an individual deviation record for that person, which can then be used to generate a person-specific deviation profile. Thus, instead of using one or more physiological parameters (for example, common CBC ordered by a physician), a differential genetic sequence object for (preferably) the entire genome of a person is compared to a reference differential genetic sequence object to so arrive at a significantly more comprehensive collection of information. Most typically, the person-specific deviation profile is then matched against normal or reference records for reference differential genetic sequence objects to so accurately and quickly identify the person as matching a specific condition or disease.

Fundamental Considerations

At first approximation, a tumor growth is a population of cancer cells. This population may homogenous, where all tumor cells share substantially the same genetic characteristics. Such tumors are said to be monoclonal since all tumor cells feature substantially the same genetic variants (e.g., copy number aberrations, structural variants, mutations) as compared to the progenitor tumor cell from which the tumor cells propagated. This progenitor tumor cell may be the first cancerous cell that initiated the tumor, or may be a subsequent tumor cell that gained an advantageous mutation that aided a complete sweep of the tumor population.

On the other hand, polyclonal tumor growths are viewed as tumors composed of at least two genetically distinct clonal populations of tumor cells. In polyclonal tumors, each clonal population arose from a respective progenitor clone, but each progenitor clone differs from the other by some observable alteration. Thus, the multiple clonal populations may be significantly different from each other, or (as is more often the case), the clonal populations are related, sharing a set of variants that are found in all or a large subset of tumor cells. For example, a polyclonal tumor may comprise multiple major clones, where a major clone represents a computationally detectable clone (typically representing 10% of the tumor population), while the same polyclonal tumor may comprise further numerous minor clones that are undetectable with any given method.

In addition, it should be noted that individual mutations may be classified as either clonal or subclonal. In that context, when the dominant clones of a particular tumor are found, clonal variants are those shared by all tumor cells of any or all dominant clones. Viewed from a different perspective, clonal variants achieved full penetrance in the entire population or polyclonal subpopulation of cells. Subclonal variants are those that exist in only a small proportion of the cells belonging to a clonal population.

Figure 1:
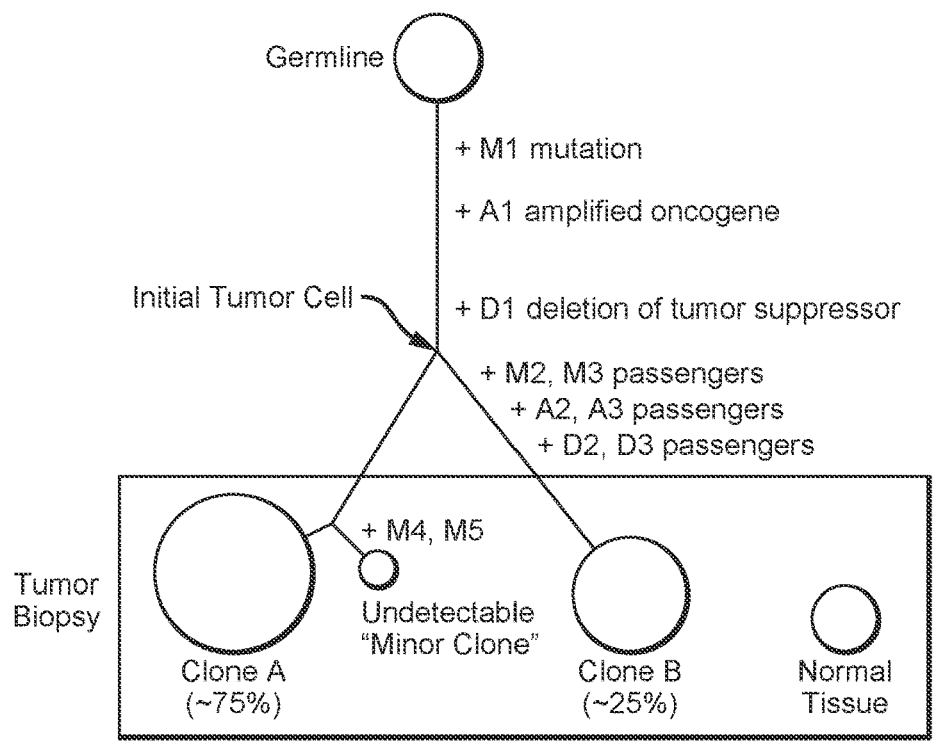
FIG. 1 is an exemplary illustration of evolution of a tumor starting from a germline cell, to an initial tumor cell, to a population of major and minor clones that are sampled by the tumor biopsy.

An example for the above model of tumor and its evolution is provided in FIG. 1 in which an initial germline cell acquired a nonsense mutation in a key tumor suppressor (M1) and amplified an oncogene (A1) that supported the initial growth of a tumor. Early on in this tumor's development, another tumor suppressor was deleted (D1) that caused the tumor cell to grow even more rapidly, enabling cells with this deletion to rapidly overtake the entire tumor population. Soon after acquiring deletion D1, a cell also acquires a set of neutral mutations (M2, M3), amplifications (A2, A3), deletions (D2, D3). Since these variants occurred early during the clonal expansion of this tumor cell variant, but do not provide any selective advantage, the population of tumor cells are split into two "major clones," where 25% of tumor cells have the neutral variants (M2, M3, A2, A3, D2, and D3) and 75% of tumor cells do not. Much further during this tumor's development, additional mutations (M4, M5) appear on one of the two major clones, but do not have a chance to spread through the population prior to the patient's death and/or tissue biopsy.

In the example of FIG. 1, the tumor population is polyclonal, with its two major clones defined such that: clone (1)

has variants M1, A1, and D1, and clone (2) shares the variants of clone (1), but in addition has variants M2, M3, A2, A3, D2, and D3. The clonal mixture is determined as 75% clone (1) and 25% clone (2). Mutations M1, M2, and M3 would all be classified as "clonal" since they all achieved full penetrance in their respective clones, while M4 and M5 would be classified as "subclonal" mutations. Moreover, as can be seen from FIG. 1, a biopsy will typically include normal tissue in addition to tumor heterogeneous tissue.

Data Extraction and Synthesis

The following presents various systems and methods to extract and synthesize data to reconstruct the clonal evolution of a tumor from whole genome sequencing data of a single tumor biopsy. These systems and methods provide a powerful framework to determine the clonality of a tumor, the number and proportion of all major clones in the tumor, and possible variants that distinguish the major clones. Furthermore, systems and methods are presented to phase mutations to parental alleles to thereby time their emergence within the population. In addition, contemplated systems and methods will provide an accurate estimate of the amount of contaminating normal tissue that was present in a tumor biopsy.

Copy Number Alterations, Allele Fraction, and the Allelic State Diagram

To discover and describe the major clones of a population, relative copy number and allele fraction estimates are utilized. Such data can be obtained using algorithms and methods as described in WO2013/074058. Underlying the method to determine both clonality and estimate normal contamination is the "allelic state diagram" (ASD), which is described in more detail below. It should be especially appreciated that the ASD describes the positions of clonal positions of allele-specific copy number variants using both relative copy number and allele fraction of copy number alterations, thus demonstrating the relationship between copy number and allele fraction for all allelic states. The positions of clonal allelic states in the ASD are determined by the following Equations I and II:

$$CN(t_{maj}, t_{min}, n_{maj}, n_{min}, \alpha) = \frac{(1-\alpha)(t_{maj} + t_{min}) + \alpha(n_{maj} + n_{min})}{n_{maj} + n_{min}} \quad \text{Eq. I}$$

$$AF(t_{maj}, t_{min}, n_{maj}, n_{min}, \alpha) = \frac{(1-\alpha)t_{maj} + \alpha n_{maj}}{(1-\alpha)(t_{maj} + t_{min}) + \alpha(n_{maj} + n_{min})} \quad \text{Eq. II}$$

where CN is the relative tumor copy number compared to a matched-normal, AF is allele fraction in the tumor, a is the fraction of normal contamination in the tumor sample, and $t_{maj}$, $t_{min}$, $n_{maj}$, and $n_{min}$ are the majority and minority allelic states in the tumor and normal, respectively. Since individual genomes can only have discrete allelic states, such that they have 0, 1, 2, or more copies of a given chromosomal segment, the possible values for $t_{maj}$ and $t_{min}$ are constrained to the set of positive integers, ti∈(0, 1, 2, ... , n). Furthermore, the majority and minority allelic states for the normal are set to one, $n_i$=1, which is true for all of the autosomes in a normal human genome. The sex chromosomes, X and Y, are ignored in the ASD. Note that since the above formulae necessarily require two alleles, only heterozygous sites in the matched normal genome are considered for the ASD.

Figure 2:
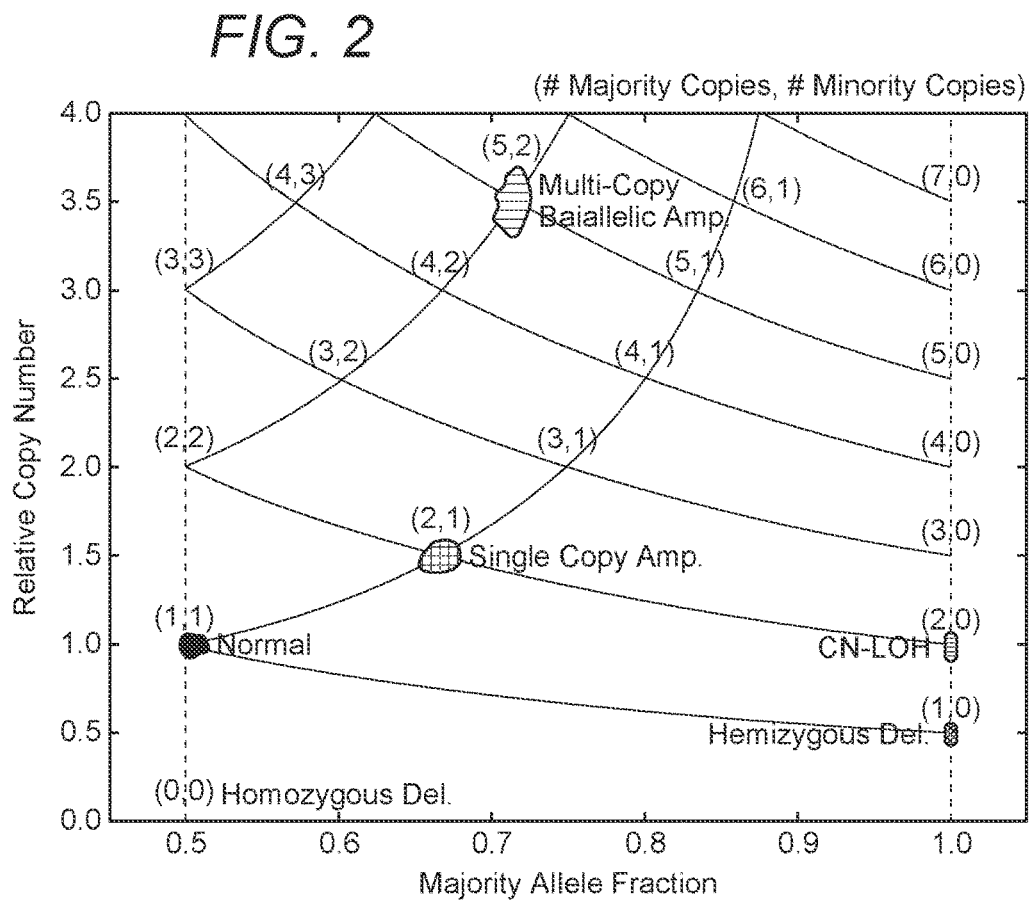
FIG. 2 is an exemplary allelic state diagram (ASD) of simulated data for a monoclonal tumor sample with zero normal contamination, $\alpha=0$. Chromosomal regions exhibiting different copy number alterations are plotted in different shades. This simulated tumor genome exhibits 6 allelic states: normal, single-copy amplification, hemizygous deletion, homozygous deletion, copy-neutral loss of heterozygosity (LOH), and multi-copy biallelic amplification. (supported by [0009]).

In the following figures, particularly significant allelic states are normal copy number, single-copy amplification, single-copy/hemizygous deletion, homozygous deletion, copy-neutral loss of heterozygosity (CN-LOH), and amplification of both parental alleles. For example, FIG. 2 shows exemplary copy number and allele fraction data for the above allelic states with no normal contamination, demonstrating how the ASD can be used to determine the allelic state of each cluster of points. Here, each vertex in the ASD's grid is labeled with its tumor allelic state, ($t_{maj}$, $t_{min}$), and the position is determined by the equations above. FIG. 3 demonstrates how the locations of allelic states are affected by increasing amounts of normal contamination, α. FIG. 3A has no normal contamination (α=0), with FIGS. 3B-D having increased normal contamination (3B: α=0.1; 3C: α=0.5; 3D: α=0.9). As is readily apparent, as normal contamination increases, the allelic state positions grow closer together, reducing the ability to resolve different allelic states. It should be especially noted that plotting the copy number versus allele fraction to produce an ASD provides various technical advantages, including the capability to observe and identify clonality status of a tumor and the capability to observe and identify (unidirectional and bidirectional) changes in the clonality status of a tumor.

Figure 4:
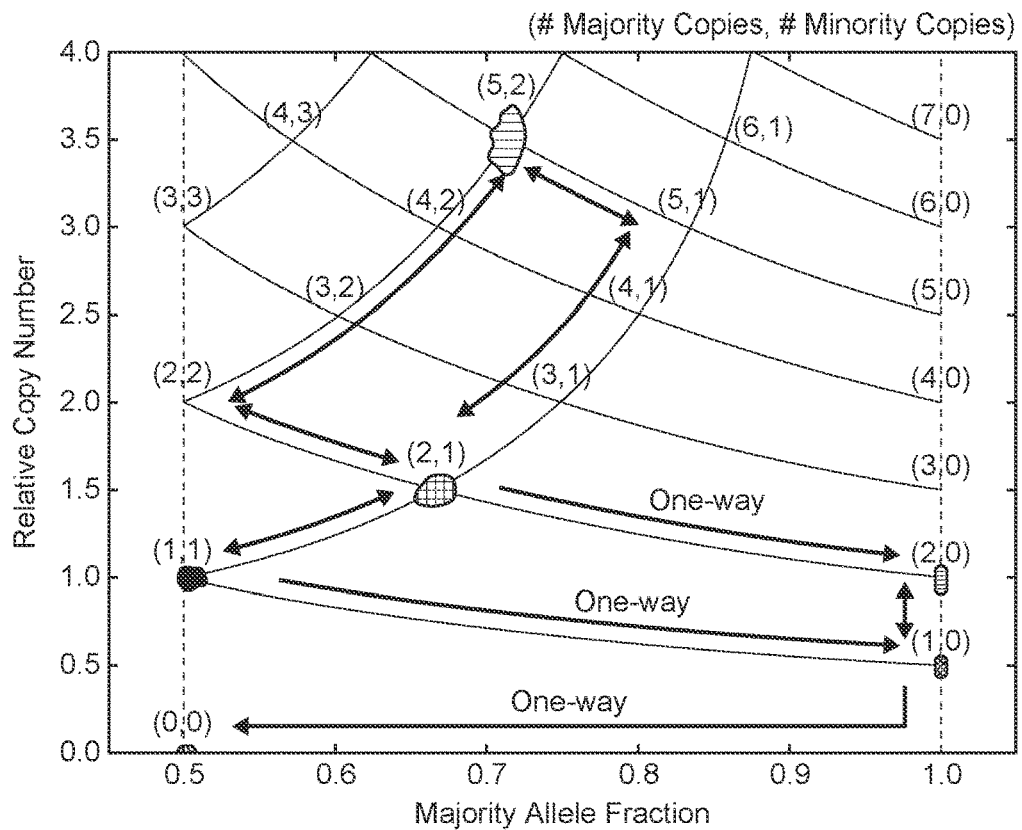
FIG. 4 is the allelic state diagram of FIG. 2 showing some possible bidirectional and unidirectional transitions between allelic states where unidirectional transitions are those that involve irreversible loss of a parental chromosome.

It should be noted that the example of FIG. 3 depicts a static snapshot of a monoclonal tumor. However, it is well known that the tumor genome can be very dynamic, with gains and losses of small and large chromosomal segments. FIG. 4 exemplarily illustrates some of the possible transitions between the allelic states described in previous figures. It should be appreciated that some transitions are "one-way" since they involve the irreversible loss of chromosomal segments. For example, the transition between the normal allelic state (1,1) and the hemizygous deletion state (1,0) is "one-way" because that deleted allele can never be restored. However, the retained allele in this case can be amplified, permitting transitions to the copy-neutral LOH (CN-LOH) state and beyond (2+,0). Notice that the deletions necessary for the transition between other allelic states are not deemed "one way" because at least one copy remains of each allele remains in the genome.

Based on the above, it should be recognized that allelic states can now be identified in a relatively simple manner. For example, FIG. 5 displays the ASD of a tumor genome transitioning from the allelic states presented in the previous figures to new allelic states that differ only by a single copy loss or gain. During such a transition, the population of tumor cells will be a mixture of tumor cells having tumor cells with the original allelic states and tumor cells with the new allelic states. For the example presented in FIG. 5, one could view this "transitional" tumor as a population divided between two major clones, A and B, where clone A is defined by the original allelic states, and clone B is defined by the new allelic states. The mixture fractions shown on this figure, $M_b$, represents the fraction of clone B within the population, such that the tumor population solely consists of clone A when $M_b$=0, and the population consists only of clone B when $M_b$=1. It is important to note that the allelic states for both clones, $t_{i,a}$ and $t_{i,b}$, are still constrained to the set of positive integers.

Figure 5:
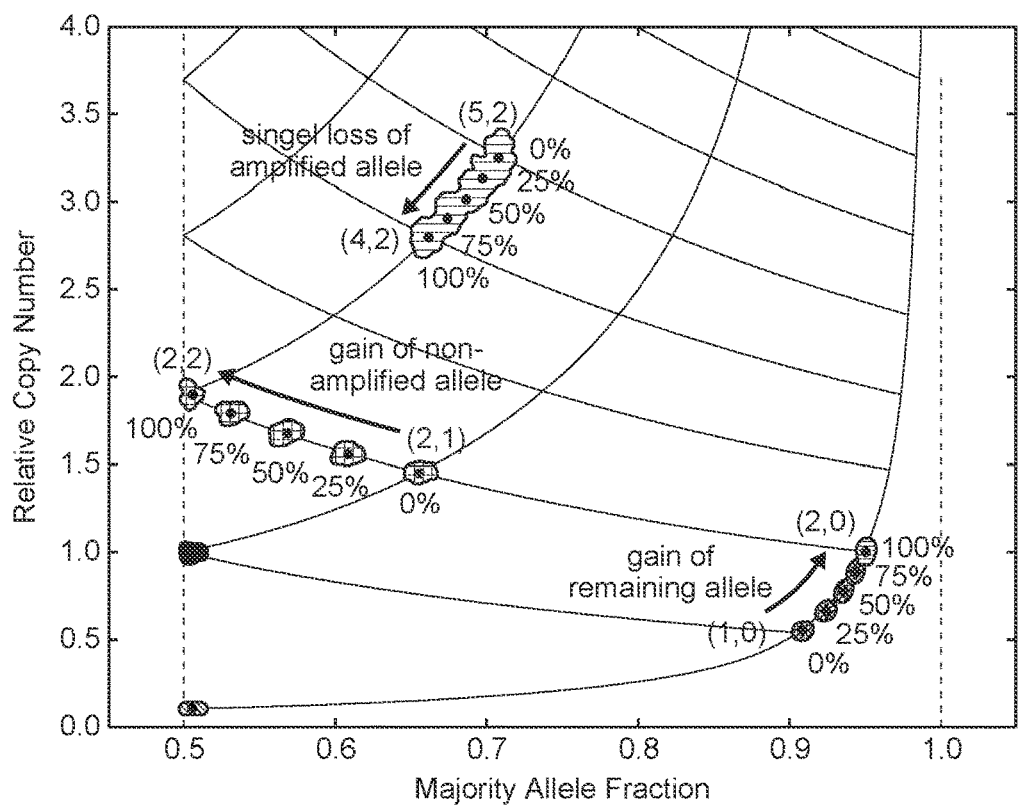
FIG. 5 is an allele state diagram for a tumor genome transitioning from the allelic states presented in the previous figures to new allelic states that differ only by a single copy loss or gain. Here, transitional allelic states are created when the tumor comprises a mixture of two different clones/subclones: Clone A is defined by the original allelic states: (2,1), (5,2), and (1,0). Clone B alters these states through amplifications and a deletion to produce the allelic states: (2,2), (4,2), and (2,0). The percentages denote the percentage of clone B present in the tumor population, where 0% describes a monoclonal population of clone A, and 100% is a monoclonal population of clone B.

From FIG. 5, when the mixture fraction $M_b$ is such that the tumor is a heterogenous population of cells, $M_b$=0.25, 0.5, 0.75, the allelic states do not lie on the vertices of the ASD, but rather on the edge connecting two vertices. A tumor population in such a state would be classified as polyclonal. Take, for example, the cluster of points in FIG. 4. In this region of the genome, clone A has the allelic state of hemizygous deletion, or (1, 0), whereas clone B has amplified clone A's retained allele, altering its allelic state in this region to copy-neutral LOH, or (2, 0). When $M_b=0$, the allelic state of the red points are found clustered on the ASD vertex representing the hemizygous deletion allelic states. As M increases (i.e. with increasing amounts of clone B in the population), the cluster of points progresses along the edge towards the CN-LOH state. At $M_b=0.5$, where there are equal amounts of clone A and B in the population, the cluster of points is found precisely in the middle of the edge between the LOH and CN-LOH allelic states.

Figure 6:
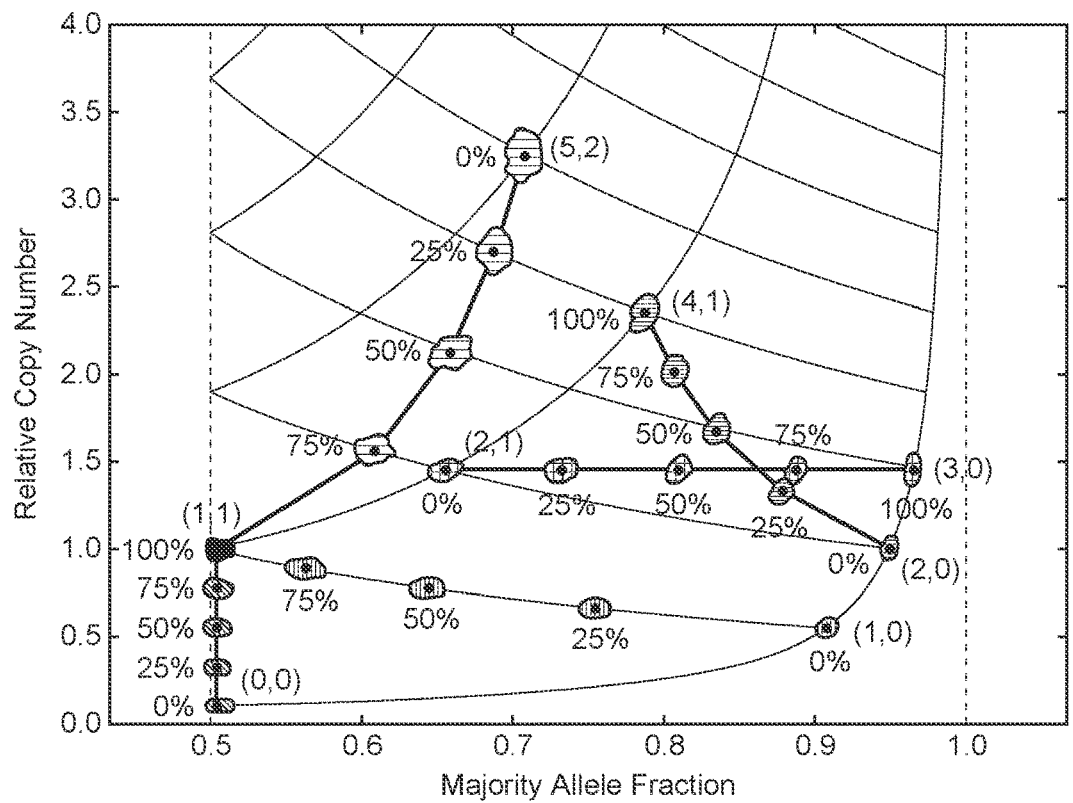
FIG. 6 is an exemplary illustration of an allelic state diagram of the FIG. 2 showing the transitional allelic states produced when allelic states are "skipped", which can occur when the tumor consists of two or more unrelated, or distantly-related clones. In that case, the transitional states are not found on the edges connecting allelic states if the allelic states of the two major clones differ in both majority and minority alleles.

If the tumor population comprises non-derivative clones, or clones that are distantly related to one another such that their allelic states do not differ by single copy gains or losses, the position of the mixture of allelic states will not lie along the edges of the ASD, as shown in FIG. 6. As will be discussed in more detail below, such abnormal allelic states can also occur when more than 2 major clones exist in a polyclonal tumor. Thus, it should be recognized that the ASD can, at a glance, indicate the presence of one or more major clones in a tumor sample, help determine the allelic states of the major clones, and provide a visual estimate of the proportion of each major clone in the tumor population, rendering the ASD a powerful diagnostic tool for determining clonality of a tumor sample. Moreover, it should be appreciated that plotting the copy number versus allele fraction to produce an allelic state diagram advantageously allows determination of mixture fractions in non-monoclonal related/derivative or unrelated/non-derivative tumors.

Fitting Sequence Data to the ASD

The mathematical construct behind the ASD is expressed in Equation I and II above is modeling the ideal case where the relative copy number is 1.0 and the majority allele fraction is 0.5 for normal (1, 1) allelic states. However, the results produced by sequence analysis on real world data do often not precisely fit this idealized case. To estimate the relative copy number, sequence analysis (e.g., as described in WO2013/074058) calculates the relative coverage between tumor and normal. If the tumor and normal samples are sequenced at the same coverage level, relative coverage is an accurate measure of relative copy number. However, this will not be the case if the tumor sample is sequenced at a much higher coverage than its matched-normal, in an attempt to improve detection of mutations, particularly subclonal mutations, in the tumor sample.

For example, and assuming no normal contamination, if a tumor is sequenced at twice the coverage of its matched-normal, then a region with a "normal" allelic state will have twice as many reads in the tumor as it has in the normal. Thus, this region has a relative coverage of 2.0 and a relative copy number of 1.0, and the so determined relative coverage will not fit the ASD. Unfortunately, the precise coverage level of a given sequencing dataset is unknown, as the sequencing services often only target the desired coverage level, but have no guarantee of achieving it. Using the raw number of reads found in the tumor and matched-normal datasets as an estimate of overall coverage level can help correct the imbalance, but is complicated by the ploidy of the tumor sample. If a tetraploid tumor (ploidy=4.0) and its matched-normal (ploidy=2.0) are sequenced at the same physical coverage, the tumor will have two times the number of raw reads than the matched-normal. So, using the ratio of their raw numbers of reads to scale local relative coverage estimates would this tetraploid tumor to appear to have normal copy number.

The error in the estimate of allele fraction that sequence analysis (e.g., as described in WO2013/074058) produces is caused by a limitation in how the majority allele is selected in regions of allelic balance, such as the "normal" allelic state. Ideally, the allele fraction for such regions should be approximately 0.5, but this only occurs when both alleles have equal read depths. More often, due to the stochastic nature of how heterozygous alleles are sampled from a pool of genomic DNA, one of the two alleles will likely have a slightly higher read depth than the other, causing a slight increase in the majority allele fraction that is estimated.

For example, assuming no normal contamination, a whole genome with 30× coverage would ideally produce 15 of both alleles at heterozygous "normal" allelic states. However, if one allele's read depth was shifted by just a single read, such that allele A has read support of 16, the sequence analysis (e.g., as described in WO2013/074058) would estimate the majority allele fraction to be 16/30=0.53, a deviation of 0.03 from the actual allele fraction. Usually averaging over multiple positions can reduce the effect of such errors, the error in majority allele fraction for these balanced allelic states cannot be averaged out because majority allele fraction, by its definition, can never dip below 0.5. Fortunately, sampling error has a much less pronounced effect on amplified and deleted allelic states. In these cases, the majority allele is readily identifiable and the sampling error can be averaged out over multiple positions.

In order to fit sequence analysis results (e.g., as described in WO2013/074058) onto the idealized ASD, the above errors can be modeled and corrected out from the data. The model has four parameters: normal contamination $\alpha$, allele fraction delta $AF_d$, coverage delta $COV_d$, and coverage scaling factor $COV_E$. The $\alpha$ parameter only affects grid layout of the ASD, as shown in FIGS. 3A-D. The latter three parameters transform the sequence analysis results. The parameters $COV_d$ and $COV_E$ affect the y-axis shift of the copy number data and scale of copy number data from the "normal" allelic state according to the following equation:

$$CN_{corr}(CN, COV_d, COV_s) = COV_s(CN - COV_d) + 1.0$$

where CN is the relative copy number estimate produced by the sequence analysis and $CN_{corr}$ is the corrected copy number used to compare against the ASD. The final parameter, $AF_d$ has its strongest effect on the allele fraction estimates of the allelic balanced states. It does this with the following equation:

$$AF_{corr}(AF, AF_d, CN_{corr}, x) = AF - \frac{AF_d}{CN_{corr}}\left(\frac{1.0 - (AF - AF_d)}{0.5}\right)^x$$

where x is set to a large integer (e.g. x=20) to rapidly reduce the degree to which allele fraction estimates are corrected as they diverge from balanced allelic states. It should be noted that the allele fraction estimates at deleted states should not be appreciably altered as they are the determining factor for estimating normal contamination.

The optimal values for these four parameters are discovered using gradient steepest descent search, optimizing the RMSD of the corrected copy number and allele fraction estimates, $CN_{corr}$ and $AF_{corr}$, to the ASD defined by the normal contamination parameter, $\alpha$. The search begins with a set of initial values for each parameter, and a set of increments for each parameter, $COV^i_d$, $COV^i_s$, $AF^i_d$ and $\alpha^i$. For each parameter, p, and parameter increment, $p^i$, the RMSD from the ASD is calculated for p, $p+p^i$ and $p-p^i$. The parameter value that yields the greatest reduction in RMSD among all four parameters is chosen as the new current value for that parameter, and the cycle repeats. If no reduction in RMSD is possible with the current parameter increments, the increments are divided by half and the search resumes.

Once three rounds of divisions have occurred, the search is concluded and the best fit parameters are reported. Since gradient descent can often get stuck in a local minimum, gradient search is performed with a number of different initial parameters until a consistent set of fit parameters is found. Therefore, it should be noted that by taking onto account the actual coverage of the sequence reads (e.g., tumor reads versus normal reads) as described above will allow to identify allelic states even where coverage between tumor and normal is not identical (or even unclear).

Modeling the Clonal Mixture of a Tumor Sample

The ASD can then be used to determine a set of allelic state "landmarks" that help define the number of distinct clones and their proportions within the tumor population, $L_i = (CN_{corr,i}, AF_{corr,i})$. The landmarks used in this analysis will be defined by the large clusters of points on the ASD, as they indicate major portions of the tumor that have undergone a copy number change in a significant fraction of the overall tumor population. See FIG. 7B for the landmark allelic states used to analyze GBM-06-0185. For each landmark on the ASD, all plausible clonal mixtures that would result in its observed copy number and allele fraction are considered, then the optimal clonal mixture is chosen such that it can account for all ASD landmarks most parsimoniously.

As observed in FIG. 5, for monoclonal tumor populations, one would expect the landmarks to all lie on ASD vertices. However, in polyclonal tumors comprising two major clones, where clone B inherits all of clone A's allelic states and has additional allelic states distinct from clone A, one would expect to find landmarks on both the vertices and edges of the ASD. The landmarks that lie on vertices are those that represent the allelic states shared by both clone A & B, while the landmarks on ASD edges represent the mixture of the different allelic states. The position along this connecting edge determines the proportions of clone A and B in the mixture. If multiple landmarks are found on edges and not on vertices, then the variety of positions along their respective edges will determine the number of clones.

For example, if all landmarks are found halfway between two allelic states, the example is most simply explained by two major clones in equivalent proportion within the population. If, however, one landmark is located at the halfway mark and another is found 25% along the way towards an allelic state, there must be more than two clones in the population. One simple explanation for this is that there are three clones, A, B, & C, where A makes up 50% of the tumor population and clones B & C make up 25% each. Assuming clones B & C both exhibit a single-copy allelic state change from clone A, explaining the halfway landmark. The 25% landmark is then explained if, in that chromosomal segment, clone B (or C) experienced a single-copy allelic state change not found in clones A and C (or B). Thus, the problem at hand is determining the least number of major clones that explain n observed landmarks, which can be expressed as:

$$L^{obs} \in (L_0^{obs}, L_1^{obs}, \ldots, L_n^{obs})$$

where $L^{obs}_i = (CN^{obs}_i, AF^{obs}_i)$. One can then assume a mixture of m clones, each with k integral majority and minority allelic states $C_i = [(t^0_{maj,i}, t^0_{min,i}), (t^1_{maj,i}, t^1_{min,i}), \ldots, (t^k_{maj,i}, t^k_{min,i})]$, and mixture proportions, $M_i$, such that $\Sigma M_i = 1.0 - \alpha$. The relative copy number and allele fraction of each landmark, $L^{mix}_i$, is a linear combination of the allelic states indexed by i across the clonal mixture:

$$CN_i^{mix} = \frac{2\alpha + \sum_k^m M_k(t^k_{maj,i} + t^k_{min,i})}{2}$$

$$AF_i^{mix} = \frac{\alpha + \sum_k^m M_k(t^k_{maj,i})}{2\alpha + \sum_k^m M_k(t^k_{maj,i} + t^k_{min,i})}$$

where the normal allelic states for all clones are assumed to be $n^k_{maj,i} = n^k_{min,i} = 1$. The optimal solution is the one that most closely approximates the observed landmarks with a simplest mixture of major clones, or optimizing the objective function:

$$O(L^{obs}, L^{mix}) = \frac{1}{n}\sqrt{\sum_i^n (CN_i^{obs} - CN_m^{mix})^2 + (AF_i^{obs} - AF_i^{mix})^2} + m^x$$

which is the RMSD from the observed data plus a penalty for the number of clones in the population, controlled by the strength parameter x.

The method is performed after finding the best fit parameters. It begins by identifying all "shared" landmark allelic states, which every clone in the mixture must exhibit. If we assume a tumor is step-wise evolving, these shared allelic states represent the "root" of the tumors evolutionary tree. If there are no landmarks on ASD edges, the procedure is complete and the tumor population is classified as monoclonal.

If landmarks exist along ASD connecting edges, between two bounding allelic states, then additional clones are necessary. The procedure adds one additional "daughter" clone to the mixture, which inherits all of the shared allelic states and gains an allelic state and mixture proportion necessary to explain the edge-bound landmark. If more than one edge-bound landmark can be explained with the same mixture proportion, then those new allelic states are added to the new clone. This process is repeated until all non-vertex landmarks are explained by the clonal mixture, wherein each additional "daughter" clone can derive from any current clone in the mixture that bounds one side of an unexplained landmark. Once all landmarks can be reasonably explained, the clones' allelic states and mixture proportions are reported.

It should be noted that from the equations above the combination of allelic states that uniquely determine each landmark's position on the ASD can also determine the phased set allelic states for all positions in the genome that correspond to the landmark. This can only work when the mixture proportions are unique for each clone, i.e. the major clones must unevenly split the tumor population. In such cases, this enables whole genome, clone-specific karyotypes to be inferred for each clone in the tumor population. Consequently, using an allelic landmark will provide a technical advantage in that it is now possible to define the number of distinct clones and their proportions within the tumor population.

Linking Mutations to Clone-Specific Allelic States

To achieve an even greater understanding of the evolution of a tumor, one need not be constrained to exclusive analysis of copy number changes. By integrating somatic mutations into the above discussed framework, it is now possible to determine when a mutation arose during the tumor's development. To do this, one or more mutations will be directly linked to the majority or minority allele in the encompassing chromosomal region on the ASD. Then the mutation's allele fraction is used to determine whether the mutation occurred prior to the change in allelic state, soon after the allelic state change, or much later. Such analysis can be performed in two different manners.

Via direct phasing: For every mutation discovered by sequence analysis, all nearby germline heterozygous variants can be identified to identify paired reads that physically connect, or "phase," the mutation allele to a specific germline allele. "Nearby" is defined in this context as being separated by no more than double the insert size of the paired read library, typically 1,000 bp for these whole genome libraries, as that is well outside the expected distance that would separate two paired reads.

All read pairs that overlap the positions of both the mutation and the germline variant are collected and the number of times the mutation is phased to either germline variant alleles is recorded. If the mutation is found linked to the same germline variant allele more than once, and is not found also phased to the other allele of that germline variant, it is considered to be directly phased to that germline variant allele. Phasing can be made either within a single read if the mutation and germline variant are separated by less than a read's length, or can occur across mates of a read pair. Mutations can also be phased to multiple germline variant positions.

For every mutation that can be directly phased to a germline variant, the germline variant's allele fraction is used to determine if the mutation is phased to the majority or minority allele. If the germline variant's allele fraction is determined to be greater than or equal to 0.5, then the mutation is deemed "majority-phased," otherwise it was phased to the minority allele, or "minority-phased." Note that in the cases of when the two allelic states are equal, such as normal (1, 1) or bi-allelic, balanced amplifications (2, 2), the mutation's assignment to "majority" or "minority" allele depends on whichever allele was sampled slightly deeper in the sequencing data. Thus, classifying mutations as "majority-phased" or "minority-phased" in such cases is not meaningful.

Via amplified allele fraction: When direct phasing cannot be made, the ability to determine which allele the mutation is linked to is severely limited. However, when mutations are found within an amplified chromosomal segment, one can use the mutation's allele fraction to determine to which allele the mutation may be linked. When the mutation's allele fraction is approximately equal to the majority allele fraction, this can only have occurred if the mutation was present in the amplified allele prior to the amplification. If the mutation was instead on the un-amplified allele, the mutation's allele fraction would necessarily be much lower.

However, low mutation allele fractions do not necessarily indicate that they are not "majority-phased," since mutations can occur post-amplification. For example, if a region was amplified by a single copy, allelic state (2, 1), a post-amplification mutation could be, at most, present on one copy of the majority allele, with a maximal allele fraction of 1/2+1=0.33, compared to the expected allele fraction of a pre-amplification mutation, 2/2+1=0.67.

Thus, one is limited to linking un-phased mutations to amplified segments when the mutations occur prior to the amplification. Nevertheless, this can be still be useful, as one would expect oncogenic mutations to occur early in the tumor's development, as they are likely to drive tumor growth. If multiple copies of these oncogenic mutations are selectively advantageous for the tumor cell, then one would expect the requisite increase in mutation copy number and allele fraction to enable the user to employ this method.

Comparing Allele Fractions to Infer Mutation Timing

After assigning mutations to the majority or minority alleles, one can then compare the allele fraction of the mutation to the allele fraction of the majority or minority allele fraction of the chromosomal segment that encompasses the germline variant allele. It is generally preferred to use the allele fraction of the chromosomal segment instead of the germline variant allele because the estimate of the chromosomal segment's allele fraction is more accurate due to averaging over all germline heterozygous positions within the segment. To accurately compare a mutation's allele fraction to the majority or minority allele fraction of heterozygous positions, one must add in some "normal" contamination to the mutated allele. Note that majority allele fraction, AF, features normal contamination in both its numerator and denominator. This is due to the fact that the positions considered in these equations are heterozygous in the normal, and thus one expects to get normal contamination from both alleles. However, for a somatic mutation, there is no normal contamination of the mutant allele, as the mutation does not exist in the normal:

$$MAF = \frac{(1-\alpha)mt_{maj}}{(1-\alpha)(mt_{maj} + (1-m)t_{maj} + t_{min}) + \alpha(n_{maj} + n_{min})}$$

where MAF is mutant allele fraction, m is the fraction of copies of the tumor allele $t_{maj}$ that are mutated, and $t_{maj}$, $t_{min}$, $n_{maj}$, and $n_{min}$ represent the same homozygous allele. To fairly compare MAF to allele fractions estimated at heterozygous positions, the following correction is employed:

$$MAF_c = MAF + \frac{\alpha n_{maj}}{(1-\alpha)(t_{maj} + t_{min}) + \alpha(n_{maj} + n_{min})}$$

$$= \frac{(1-\alpha)mt_{maj} + \alpha n_{maj}}{(1-\alpha)(t_{maj} + t_{min}) + \alpha(n_{maj} + n_{min})}$$

where MAFc is the corrected mutant allele fraction. Note that while m is allowed to be any fraction less than or equal to zero in the above equations, there are some values of m that have special meaning. If m=1, then all of the $t_{maj}$ alleles were mutated, and in the cases where $t_{maj}$ represents an amplified allele, when m=1 the mutation must have occurred prior to the amplification. When m=1 $t_{maj}$, where $t_{maj}$ represents the number of copies of the amplified allele, then one knows that the mutation must have occurred soon after the amplification, since it exists on a single copy of the amplified allele but is found in this state in the majority of tumor cells. If, however, m<<1/$t_{maj}$, then the mutation must have occurred after the amplification, likely very late during the tumor's growth, as its very low allele fraction indicates it's only found in a small fraction of tumor cells.

If the mutation is phased to the minority allele, $t_{min}$, one expects to find the maximum mutation fraction to be m=$t_{min}$/$t_{maj}$ as that indicates that all copies of the minority allele were converted. So, when the minority allele state exists in single copy and all copies of it were mutated, m=1 $t_{maj}$, precisely the same mutant fraction one would calculate for a "majority-phased" mutation present at single copy. Thus, only with the direct phasing one can distinguish between an early "minority-phased" mutation and mutations that occur post-amplification.

Examples

GBM (Glioblastoma Multiforme):

12 whole genome GBM samples were processed with the above methods to determine the level of normal contamination and the clonality present in each tumor biopsy. The relative coverage and allele fraction produced by BamBam for the other 5 whole genome GBM samples discussed in previous sections possessed too much variability to be analyzed by these methods. The results of the clonality analysis are summarized in Table 1.

| Sample | Clonality | Normal Cont. ($\alpha$) | # Major Clones |
|---|---|---|---|
| GBM-06-0145 | monoclonal | 22.5% | 1 |
| GBM-06-0155 | monoclonal | 24.5% | 1 |
| GBM-06-0877 | monoclonal | 29.8% | 1 |
| GBM-06-0648 | polyclonal | 12.5% | 2 |
| GBM-06-0152 | polyclonal | 24.1% | 3 |
| GBM-06-1086 | polyclonal | 7.5% | 4 |
| GBM-06-0185 | polyclonal | 14.6% | 4 |
| GBM-14-1454 | polyclonal | 5.9% | >1 |
| GBM-14-0786 | polyclonal | 13.9% | >1 |
| GBM-06-0188 | polyclonal | 20.6% | >1 |
| GBM-06-0214 | polyclonal | 33.6% | >1 |
| GBM-26-1438 | polyclonal | 50.0% | >1 |

Surprisingly, only 3 GBM tumor samples were found to be monoclonal, while the other 9 samples included at least two major clones. For 7 GBM tumors, the precise mixture of clones was determined, while the remaining 5 tumor were inspected visually to determine their clonality.

Results of two tumors, GBM-06-0145 and GBM-06-0185, are shown in FIGS. 7A and 7B. The relative coverage and allele fraction data of these two samples were transformed using the best fit parameters as described above, demonstrating close fit to the ASD with estimated normal contamination levels of 21.5% and 14.6%, respectively. By inspecting the location of the data cluster, whether on vertices or edges, one can visually determine the clonality of these tumors. Since all of GBM-06-0145's (FIG. 7A) data cluster around ASD vertices, it is likely this tumor is monoclonal. On the other hand, GBM-06-0185 (FIG. 7B) is clearly polyclonal, since the several large clusters along the ASD edges indicate the presence of at least two major clones in this tumor. In fact, since the edge-bound clusters are found at different positions along their edges (e.g. some clusters are at the halfway mark, while other clusters are approximately 0.75 and 0.80 of the way towards the single-copy deletion state, respectively), this can only occur from a mixture of at least three major clones.

To determine precisely the number of clones in these samples, the inventors used the methods described above to determine the number of clones and their allelic states. For each inferred clonal mixture, the inventors computationally determined relative copy number and allele fraction for every position in the genome given the derived clonal mixture and compared it against the results produced by the sequence analysis. This provides a metric to determine how well the clonal mixture models the observed data.

As shown in FIG. 8, the inventors found a single clone for GBM-06-0145, as expected. The computationally-derived relative copy number and allele fraction data shows a very good fit to the observed data. A total of four major clones were found for GBM-06-0185, whose clonal allelic state is presented in FIG. 9. There are two important things to note from the four clones presented here. Firstly, as described before, the fact that each clone's mixture proportion is different from all others helps to phase the allelic states across the whole genome into clone-specific karyotypes. Secondly, all clones appear to have derived from clone A. Each derivative clone shares all of the events found in clone A, suggesting that clone A is the progenitor of clones B, C, and D. It is unclear, however, if this set of clones evolved linearly, in a stepwise progression, or if clone B and clones C & D represent different lineages. These latter three clones differ by the deletions in chr6q, where clone B features a set of focal deletions while clones C & D have lost all of chr6q. These are not mutually exclusive events, so it is possible that clone C had derived from B, inheriting its focal deletions and subsequently deleting the remainder of chr6q. However, nothing precludes clones B and C from deriving directly from clone A and independently deleting parts of chr6q. It is interesting that it is clone D, the last clone of the tree, that becomes the dominant clone in the tumor population according to mixture proportion, suggesting that the events unique to this clone (e.g. amplification of chr9) may have provided a growth advantage to this clone.

The clonal karyotypes for GBM-06-0152 is shown in FIG. 10. This tumor is interesting because the amplification of chr7, a characteristic of approximately 40% of GBM tumors, does not occur until clone B. It should be noted that this sample was also shown in an independent analysis to have two double minute chromosomes, one with MDM2 & CDK4 and another containing EGFR, that were borne out of a chromothripsis-like event. While extremely amplified genomic regions are difficult to model in these clonal karyotypes, evidence of the deletions related to these events on chr12 in clone A can be seen, suggesting that these double minutes occurred early in the tumor development. It is possible that the early focal amplification of EGFR may have played a role in the later emergence of chr7 amplification.

The clonal evolution presented by the karyotypes for sample GBM-06-1086 has a few interesting aspects that are worth describing here. The first subtle thing to notice in its karyotype, shown in FIG. 11, is that the focal deletion of CDKN2A occurs does not occur until clone B, suggesting it occurred after the complete loss of chr9 observed first in clone A. This is strong evidence supporting the hypothesis that focal losses of CDKN2A likely occur after arm-level or entire chromosomal losses of chr9. The second interesting aspect is that clones C and D have losses of 13 different entire chromosomes. Clone D takes this one step further by deleting its last copy of chr18, as well as amplifying chr19. This reduces the ploidy of both clones C and D to 1.31, from the approximately normal ploidy shared by the other two clones (ploidy=1.95). It is remarkable how cells that have lost almost 30% of their genomic content can not only survive but, given the 41.8% mixture proportion of clone D, apparently thrive in a population of tumor cells.

Lung Squamous Cell Carcinoma (LUSC):

Whole genome data for nine squamous cell carcinomas of the lung (LUSC) sequenced by TCGA were analyzed by these methods to infer clonality. The allelic state diagrams of two tumors are shown in FIGS. 7C and 7D. From the greater number of transitional allelic states evident in these two samples, it appears that these LUSC tumors exhibit a much higher degree of clonality compared to the GBM tumors described above.

The tumor sample LUSC-66-2756 shown in FIG. 7D exhibits numerous highly amplified states at ASD vertices (states common among all major clones) and ASD edges (states shared by only a subset of major clones). A wide variety of mixture proportions is evident from the almost continuous set of different positions of point clusters along, and in between, ASD edges, suggesting that this sample is highly polyclonal. Another interesting feature of this sample is that none of its genome is found in the single copy loss allelic state (1,0). This may have occurred via a genome doubling event where the tumor genome was briefly tetraploid (N=4), then a series of chromosomal deletions led to either single copy gain, "normal," or CN-LOH allelic states. Genome doubling events are believed to often occur in serous ovarian carcinomas to explain how large portions of their genomes are observed in the CN-LOH allelic state.

Phased Mutations to Allelic States:

To visualize the phased mutations onto allelic states, the inventors used a slightly modified allelic state diagram, the dual allelic state diagram (dual ASD). Noting from the equations above that since minority allele fraction is the complement of majority allele fraction ($AF_{min}=1.0-AF_{maj}$), one can construct a dual ASD by placing a minor image of the ASD to display the location of the minority allelic states. Mutations phased to germline variants corresponding to the majority allele, minority allele, or neither, are plotted on the dual ASD. By determining which allelic state (majority or minority) the mutations are nearest and using their phased status (if any), one can infer the timing of the mutations.

An exemplary dual ASD is shown in FIG. 12, which presents a series of mutations that are phased to germline variants belonging to either the majority or minority alleles in two different allelic states. Each mutation's allele fraction is corrected as noted above and placed onto the dual ASD. Based on their phase and mutant allele fraction, the dual ASD assists in the identification on how many copies of the majority (or minority) alleles the mutation is present. In the case of the amplification presented in FIG. 12, mutations present on both alleles versus those on just one of the amplified copies is readily distinguished, allowing visual determination whether a mutation occurred before or after the amplification. Similarly, for mutations phased to the minority allele, one would see them having MAFc≤0.5 for all but the "normal" allelic state where their phased assignment is not meaningful.

The dual ASDs for tumor GBM-06-0145 are shown in FIG. 13. 6 regions on these diagrams are highlighted to help with interpretation of these diagrams on real data. Regions (a) and (b) show mutations that were directly phased via nearby germline variants to the majority allele, but only 2 mutations in (b) are found to have the MAFc corresponding to an amplified mutation. Most majority-phased mutations are found in region (a), corresponding to mutations at single copy number, discovering that these mutations occurred post-amplification. An unphased, missense mutation in DOCK8 is found in the single copy loss allelic state, meaning that the only copy of DOCK8 remaining in this tumor is in mutated state. Inactivation of DOCK8 through homozygous deletion has been linked to progression of lung cancers, so the lack of wildtype DOCK8 in this GBM tumor may have played a role in its tumorigenesis. FIG. 13 also demonstrates the high degree of variation in estimates of MAFc from these average coverage whole genomes.

The most striking thing about the dual ASD for tumor LUSC-34-2596, shown in FIG. 14, is the sheer number of mutations, phased or unphased, across all expected allelic states. Compared to the previous GBM tumor, it is clear that the mutation rate of LUSC-34-2596 is significantly higher. This is expected since lung tumors exhibit some of the highest mutation rates among the cancers studied thus far by TCGA.

The inventors observed a great number of both majority- and minority-phased mutations in the balanced-amplified allelic state (2,2) at the expected MAFc≈0.5, labeled (a) and (b) in FIG. 14. The inventors also observed a cluster of mutations to the left of these regions that corresponding to mutations at single copy number. The location of a majority-phased missense mutation in NDRG1, a gene recently discovered to be up-regulated in squamous cell lung cancer, is found in a genomic region in between the "normal" and single copy loss allelic states. Its MAFc is approximately equal to the allele fraction of the genomic region, suggesting that the mutation exists on both clones (i.e. the clone with "normal" allelic state and the clone with single copy loss allelic state). This is evidence that the mutation occurred early, prior to the emergence of the second clone featuring the new deletion, and that the deletion contained the wild-type version of NDRG1.

The location of three unphased mutations, BRAF, DNMT3A, and TP53, are also highlighted in FIG. 14. The nonsense mutation in TP53 is found in a CNLOH state and has a mutant allele fraction that precisely corresponds to the CN-LOH allele fraction, meaning that this tumor has deleted one copy of TP53, knocked out the remaining copy via mutation, and then amplified the mutant allele. The region encompassing BRAF was highly amplified, and it is clear from BRAF's MAFc that the mutation occurred prior or early in its amplification. BRAF mutations occur frequently in melanomas but have been recently discovered in a small percentage of non-small cell lung carcinomas. Since more than half of the copies are mutated, the mutation could not have occurred after the amplification process had finished unless BRAF was independently and identically mutated on multiple copies, a highly improbable event. DNMT3A, a gene whose loss is implicated in lung cancer and other tumor types, is found in the "normal" allelic state and has the expected MAFc 0.5. In all of these cases, mutations to these genes must have occurred early during tumorigenesis as they are present in all (or, in the case of BRAF, at least the majority) of the tumor's major clones. Coupled with the fact that these are genes known to be implicated in multiple tumor types raise the possibility that one or more of these mutations are drivers of this particular tumor.

Table 2 below summarizes the phaseable mutations for 12 GBM and 8 LUSC tumors. Again, the higher overall rate of mutations in the LUSC tumors relative to the GBM tumors should be noted. Also, it is clear that significantly more mutations are found at single copy within the amplified regions of the GBM tumors, whereas one can find mutations uniformly distributed across the amplified allelic states in LUSC tumors.

| Sample | Total | Maj-Phased | Amp. State | Single Copy | Min-Phased |
| --- | --- | --- | --- | --- | --- |
| GBM-06-0188 | 1,595 | 67 | 2 | 1 (50%) | 19 |
| GBM-06-0648 | 1,600 | 68 | 9 | 5 (56%) | 34 |
| GBM-06-0877 | 4,792 | 367 | 130 | 84 (65%) | 145 |
| GBM-14-1454 | 2,539 | 291 | 55 | 38 (69%) | 80 |
| GBM-06-0152 | 2,896 | 269 | 47 | 35 (74%) | 80 |
| GBM-26-1438 | 2,820 | 239 | 36 | 32 (89%) | 86 |
| GBM-06-0155 | 7,167 | 1,108 | 99 | 93 (94%) | 440 |
| GBM-06-0214 | 2,827 | 237 | 31 | 29 (94%) | 83 |
| GBM-06-0145 | 3,800 | 511 | 56 | 53 (95%) | 225 |
| GBM-14-0786 | 5,863 | 783 | 117 | 114 (97%) | 241 |
| GBM-06-1086 | 3,993 | 412 | 10 | 10 (100%) | 129 |
| GBM-06-0185 | 1,195 | 20 | 2 | 2 (100%) | 14 |
| LUSC-66-2756 | 45,995 | 7,336 | 6,869 | 2,107 (31%) | 2,104 |
| LUSC-56-1622 | 19,343 | 3,159 | 286 | 99 (35%) | 1,016 |

-continued

| Sample | Total | Maj-Phased | Amp. State | Single Copy | Min-Phased |
|---|---|---|---|---|---|
| LUSC-60-2695 | 6,265 | 830 | 408 | 148 (36%) | 302 |
| LUSC-43-3394 | 18,905 | 4,162 | 694 | 267 (38%) | 1,184 |
| LUSC-66-2757 | 11,400 | 1,477 | 374 | 177 (47%) | 498 |
| LUSC-60-2713 | 21,337 | 4,290 | 503 | 262 (52%) | 1,207 |
| LUSC-34-2596 | 30,794 | 7,166 | 663 | 349 (53%) | 1,410 |
| LUSC-60-2722 | 32,485 | 5,101 | 504 | 319 (63%) | 1,682 |

"Total" = # phased and unphased mutations called, "Maj-Phased" = # majority-phased mutations, "Amp. State" = # majority-phased mutations in regions of amplified allelic state, "Single Copy" = # majority-phased mutations in regions of amplified allelic state, but has $MAF_c$ corresponding to single copy, "Min-Phased" = # minority-phased mutations.

Assuming the mutation rate remained constant throughout the development of these tumors, then the amplifications occurred early in the development of the GBM tumors, before most mutations occurred. Using this same reasoning, mutations and copy number alterations are frequent occurrences of LUSC tumor development, with large numbers of mutations occurring prior to and after amplification events.

Another possibility explaining the difference in mutation patters is that the mutation rate did not remain constant during development. Suppose that amplification of the growth factor EGFR, a common event in these GBM tumors, increases the cell's rate of growth and subsequently reduces the cell's ability to correct mistakes made during genome replication, thereby increasing the mutation rate per cellular division. This could explain the enrichment of mutations present in single copy within amplified allelic states. However, without knowledge of the number of generations that occurred before and after EGFR amplification, one cannot determine if the mutation rate increased. Nevertheless, it should be appreciated that using the ASD and dual ASD methods presented herein, significant and clinically relevant information can be drawn from sequence analysis output that in an unprecedented manner.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer implemented method of ex-vivo determining clonality of a tumor using whole genome sequencing data obtained from the tumor, comprising:
    storing in a non-transitory, computer readable memory of a BAM server, whole genome sequence data from a first and second tissue sample of a patient; wherein the first tissue sample is a tissue sample from the tumor, and the second tissue sample is a matched normal tissue sample;
    generating, by the BAM server, a plurality of genetic sequence strings from the whole genomic sequence data of the first and second tissue sample
    incrementally synchronizing, by the BAM server, the genetic sequence strings using one or more known positions of at least one of corresponding genetic sequence strings to so produce a plurality of local alignments;
    analyzing, by the BAM server, the so produced plurality of local alignments to generate a plurality of local differential strings between the first and second sequence strings within the local alignments;
    generating, by the BAM server, a plurality of differential sequence objects for the genome from the plurality of local differential strings, wherein differential sequence objects comprise a copy number and an allele fraction for an allele within the tumor genome;
    calculating an allelic state for the allele based on the determined copy number and the determined allele fraction;
    using the allelic state to determine clonality;
    wherein the calculating the allelic state comprises at least one of a correction for normal contamination and an identification of a mixture fraction Mb for an allele, wherein the tumor is polyclonal when $M_b$ for the allele is greater than 0 and smaller than 1;
    identifying a clone of an initial tumor mass or a clone that is set to become a dominant clone using the clonality.

2. The method of claim 1, wherein the allelic state is identified as being a state selected from the group consisting of: a normal copy number, a single copy amplification, a single copy/hemizygous deletion, loss of heterozygosity followed by one or more amplifications of the remaining allele, and an amplification of both alleles.

3. The method of claim 1, wherein the step of calculating the allelic state comprises the correction for normal contamination.

4. The method of claim 1, wherein the step of calculating the allelic state uses majority and minority allelic states for tumor and normal.

5. The method of claim 1, wherein the tumor is monoclonal when $M_b$ for the allele is either 0 or 1.

6. The method of claim 1, wherein the step of calculating the allelic state comprises a correction for sequencing coverage level.

7. The method of claim 1, further comprising a step of determining an allelic state landmark.

8. The method of claim 7, further comprising a step of using the allelic state landmark to determine at least one of a number of clones in the tumor and a proportion of clones in the tumor.

9. The method of claim 1, further comprising a step of linking a mutation to a majority allele or a minority allele, and using the mutational allele fraction for determination of timing of the mutation relative to a change in allelic state.

10. The method of claim 1, further comprising a step of plotting the allelic state in an allelic state diagram.

11. The method of claim 1, further comprising a step of plotting the allelic state in a dual allelic state diagram.

12. The method of claim 1, further comprising:
    identifying a clone as the progenitor clone of other clones of the tumor.

13. A computer implemented method for providing treatment information for treatment of a tumor, comprising:
    storing in a non-transitory, computer readable memory of a BAM server, whole genome sequence data from a first and second tissue sample of a patient; wherein the first tissue sample is a tissue sample from the tumor, and the second tissue sample is a matched normal tissue sample;

generating, by the BAM server, a plurality of genetic sequence strings from the whole genomic sequence data of the first and second tissue sample incrementally synchronizing, by the BAM server, the genetic sequence strings using one or more known positions of at least one of corresponding genetic sequence strings to so produce a plurality of local alignments;

analyzing, by the BAM server, the so produced plurality of local alignments to generate a plurality of local differential strings between the first and second sequence strings within the local alignments;

generating, by the BAM server, a plurality of differential sequence objects for the genome from the plurality of local differential strings, wherein differential sequence objects comprise a copy number and an allele fraction for an allele within the tumor genome;

ascertaining allelic state for the tumor, wherein the ascertaining the allelic state information comprises generating an allele state diagram and determining location of the allelic state for the allele in the allele state diagram;

identifying presence or emergence of (a) a clone or (b) an evolutionary pattern of clones within the tumor that is indicative of at least one of susceptibility of the tumor to treatment with a drug and an increased risk of drug resistance.

14. The method of claim 13, wherein the step of identifying presence or emergence is based on prior treatment data or a priori known data.

15. The method of claim 13, further comprising:
identifying, using the allele state diagram, at least one clone as the progenitor clone of other clones of the tumor.

16. The method of claim 13, wherein the treatment targets the alteration specific to the clone that is most upstream in the evolutionary pattern.

* * * * *